(12) United States Patent
Matsuzaki

(10) Patent No.: US 9,781,931 B2
(45) Date of Patent: Oct. 10, 2017

(54) PLANT DISEASE CONTROL COMPOSITION AND ITS USE

(71) Applicant: SUMITOMO CHEMICAL COMPANY, LIMITED, Tokyo (JP)

(72) Inventor: Yuichi Matsuzaki, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 14/906,307

(22) PCT Filed: Jul. 15, 2014

(86) PCT No.: PCT/JP2014/069266
§ 371 (c)(1),
(2) Date: Jan. 20, 2016

(87) PCT Pub. No.: WO2015/012243
PCT Pub. Date: Jan. 29, 2015

(65) Prior Publication Data
US 2016/0165890 A1 Jun. 16, 2016

(30) Foreign Application Priority Data

Jul. 22, 2013 (JP) .................. 2013-151419

(51) Int. Cl.
| | |
|---|---|
| *A01N 43/713* | (2006.01) |
| *A01N 37/24* | (2006.01) |
| *A01N 43/10* | (2006.01) |
| *A01N 43/32* | (2006.01) |
| *A01N 43/40* | (2006.01) |
| *A01N 43/56* | (2006.01) |
| *A01N 43/60* | (2006.01) |
| *A01N 45/02* | (2006.01) |
| *A01N 37/18* | (2006.01) |
| *A01N 43/78* | (2006.01) |

(52) U.S. Cl.
CPC .......... *A01N 43/713* (2013.01); *A01N 37/18* (2013.01); *A01N 43/10* (2013.01); *A01N 43/32* (2013.01); *A01N 43/40* (2013.01); *A01N 43/56* (2013.01); *A01N 43/60* (2013.01); *A01N 43/78* (2013.01)

(58) Field of Classification Search
CPC combination set(s) only.
See application file for complete search history.

(56) References Cited

U.S. PATENT DOCUMENTS

| | | | |
|---|---|---|---|
| 6,369,221 B1 | 4/2002 | Hardy et al. | |
| 7,056,941 B1 * | 6/2006 | Muller ................. | A01N 43/653 514/384 |

FOREIGN PATENT DOCUMENTS

| | | |
|---|---|---|
| CN | 1265109 A | 8/2000 |
| CN | 101484009 A | 7/2009 |
| EP | 2604117 A1 | 6/2013 |
| JP | 2001-510840 A | 8/2001 |
| JP | 2014-15470 A | 1/2014 |
| WO | WO 99/05139 A1 | 2/1999 |
| WO | WO 2007-128756 | * 11/2007 |
| WO | WO 2013/092224 A1 | 6/2013 |
| WO | WO 2013/162072 A1 | 10/2013 |

OTHER PUBLICATIONS

English Translation of the International Search Report issued in the corresponding International Application No. PCT/JP2014/069266 dated Sep. 16, 2014.
International Preliminary Report on Patentability and an English translation of the Written Opinion of the International Searching Authority issued in the corresponding International Application No. PCT/JP2014/069266 dated Feb. 4, 2016.
Chinese Office Action and Search Report, with an English translation thereof, for Chinese Application No. 201480051285.X, dated Dec. 1, 2016.
Extended European Search Report for European Application No. 14829428.3, dated Nov. 21, 2016.
Examination Report No. 1 issued in the corresponding Australian Patent Application No. 2014294143 dated Feb. 15, 2017.
The Second Office Action (including an English translation thereof) issued in the corresponding Chinese Patent Application No. 201480051285.X on Jul. 12, 2017.

* cited by examiner

*Primary Examiner* — John Pak
(74) *Attorney, Agent, or Firm* — Birch, Stewart, Kolasch & Birch, LLP

(57) ABSTRACT

A composition for controlling plant diseases comprising a tetrazolinone compound represented by a formula (1):

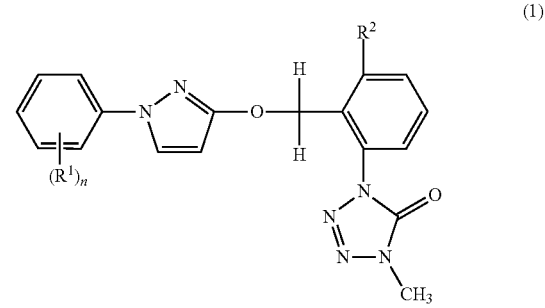

wherein n is an integer of any one of 0 to 5; $R^1$ represents a halogen atom and the like; $R^2$ represents a C1-C3 alkyl group and the like; the $R^1$ or $R^2$ can have independently halogen atom(s) in the alkyl moiety; with the proviso that when n is an integer of 2 or more, two or more of the $R^1$ may be different from each other, and an carboxamide compound, preferably the composition for controlling plant diseases wherein a weight ratio of the tetrazolinone compound to the carboxamide compound is that of the tetrazolinone compound/the carboxamide compound=0.1/1 to 10/1, shows an excellent controlling efficacy on plant diseases.

5 Claims, No Drawings

PLANT DISEASE CONTROL COMPOSITION AND ITS USE

TECHNICAL FIELD

This application claims priority to and the benefit of Japanese Patent Application No. 2013-151419, filed Jul. 22, 2013, the entire contents of which is incorporated herein by reference.

The present invention relates to a plant disease control composition and its use.

BACKGROUND ART

Hitherto, for controlling plant diseases, many compounds have been developed and used practically (see, Patent Literatures 1 and 2).

CITATION LIST

Patent Literature

Patent Literature 1: WO 99/05139 pamphlet
Patent Literature 2: WO 2013/092224 pamphlet

SUMMARY OF INVENTION

Problems to be Solved by Invention

An object of the present invention is to provide a composition having an excellent control efficacy on plant diseases.

Means to Solve Problems

The present inventors have intensively studied to find out a composition having an excellent control efficacy on plant diseases. As a result, they have found that a composition for controlling plant diseases comprising a tetrazolinone compound represented by the following formula (1) and one or more carboxamide compounds selected from the below-mentioned Group (A) has an excellent control efficacy on plant diseases.

Specifically, the present invention includes the followings:

[1] A composition for controlling plant diseases comprising a tetrazolinone compound represented by a formula (1):

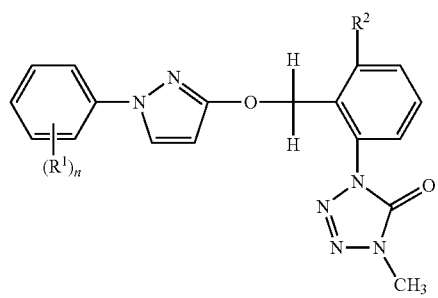

wherein
n is an integer of any one of 0 to 5;
$R^1$ represents a halogen atom, a C1-C6 alkyl group, a C1-C6 alkoxy group, a C1-C6 alkylthio group, a nitro group or a cyano group;
$R^2$ represents a C1-C3 alkyl group, a C3-C4 cycloalkyl group, a halogen atom, a C1-C3 alkoxy group, a C1-C2 alkylthio group, a C2-C3 alkenyl group, or a C2-C3 alkynyl group,
the $R^1$ or $R^2$ can have independently halogen atom(s) in the alkyl moiety;
with the proviso that when n is an integer of 2 or more, two or more of the $R^1$ may be different from each other, and one or more carboxamide compounds selected from the Group (A):

Group (A): a group consisting of bixafen, benzovindiflupyr, fluxapyroxad, penthiopyrad, N-(1,1,3-trimethylindan-4-yl)-1-methyl-3-difluoromethylpyrazole-4-carboxylic acid amide, a compound represented by the following formula (b):

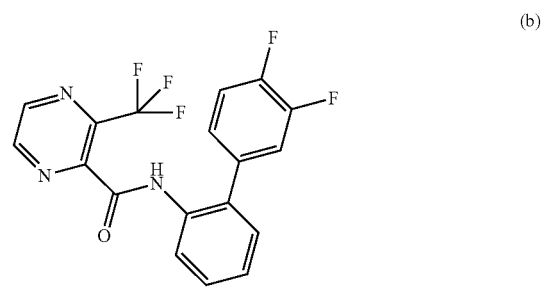 [SMILES: O=C(Nc1ccccc1-c1ccc(F)c(F)c1)c1nccnc1C(F)(F)F]

isofetamid, isopyrazam, boscalid, fluopyram, sedaxane, penflufen, flutolanil, mepronil, carboxin, thifluzamide, and furametpyr.

[2] The composition for controlling plant diseases described in [1] wherein a weight ratio of the tetrazolinone compound to the carboxamide compound is that of the tetrazolinone compound/the carboxamid compound=0.1/1 to 10/1.

[3] A method for controlling plant diseases which comprises applying each effective amount of a tetrazolinone compound represented by a formula (1):

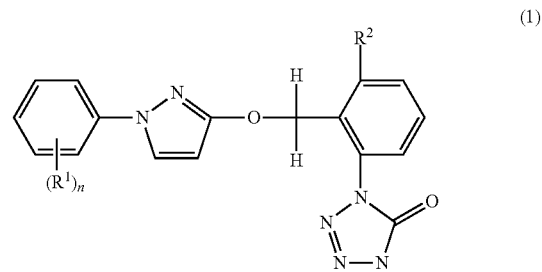

wherein
n is an integer of any one of 0 to 5;
$R^1$ represents a halogen atom, a C1-C6 alkyl group, a C1-C6 alkoxy group, a C1-C6 alkylthio group, a nitro group or a cyano group;
$R^2$ represents a C1-C3 alkyl group, a C3-C4 cycloalkyl group, a halogen atom, a C1-C3 alkoxy group, a C1-C2 alkylthio group, a C2-C3 alkenyl group, or a C2-C3 alkynyl group,
the $R^1$ or $R^2$ can have independently halogen atom(s) in the alkyl moiety;

with the proviso that when n is an integer of 2 or more, two or more of the $R^1$ may be different from each other, and one or more carboxamide compounds selected from the Group (A):

Group (A): a group consisting of bixafen, benzovindiflupyr, fluxapyroxad, penthiopyrad, N-(1,1,3-trimethylindan-4-yl)-1-methyl-3-difluoromethylpyrazole-4-carboxylic acid amide, a compound represented by the following formula (b):

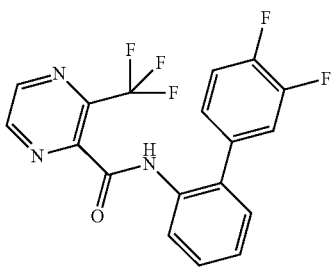

(b)

isofetamid, isopyrazam, boscalid, fluopyram, sedaxane, penflufen, flutolanil, mepronil, carboxin, thifluzamide, and furametpyr, to a plant or a soil for cultivating the plant.

[4] The method for controlling plant diseases described in [3] wherein a weight ratio of the tetrazolinone compound to the carboxamide compound is that of the tetrazolinone compound/the carboxamide compound=0.1/1 to 10/1.

[5] The method for controlling plant diseases described in [3] or [4] wherein the plant or the soil for cultivating the plant is wheat or the soil for cultivating wheat, respectively.

MODE FOR CARRYING OUT THE INVENTION

A composition for controlling plant diseases (hereinafter, referred to as "composition of the present invention") comprises a tetrazolinone compound represented by a formula (1):

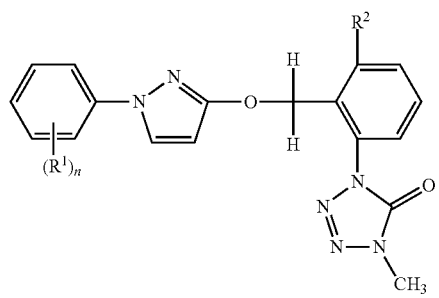

(1)

[wherein
n, $R^1$ and $R^2$ are the same as defined above, respectively.]
(hereinafter referred to as "present tetrazolinone compound")
and one or more carboxamide compounds selected from the Group (A) (hereinafter, referred to as "present carboxamide compound")

Group (A): a group consisting of bixafen, benzovindiflupyr, fluxapyroxad, penthiopyrad, N-(1,1,3-trimethylindan-4-yl)-1-methyl-3-difluoromethylpyrazole-4-carboxylic acid amide, a compound represented by the following formula (b):

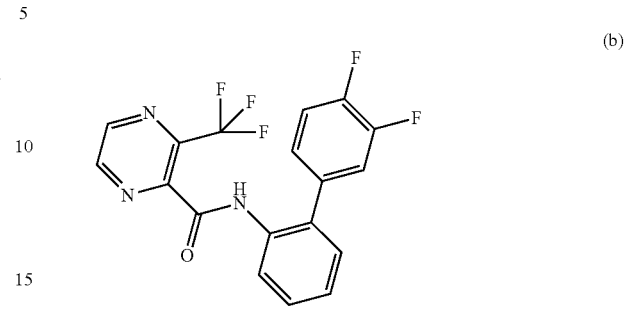

(b)

isofetamid, isopyrazam, boscalid, fluopyram, sedaxane, penflufen, flutolanil, mepronil, carboxin, thifluzamide, and furametpyr.

The present tetrazolinone is explained.

The substituent(s) as described herein is/are described in detail as below-mentioned.

The term "halogen atom" as used herein includes a fluorine atom, a chlorine atom, a bromine atom, and an iodine atom.

The term "C1-C6 alkyl group" as used herein represents a straight- or branched-chain hydrocarbon group having 1 to 6 carbon atoms, and includes, for example, a methyl group, an ethyl group, a propyl group, an isopropyl group, a butyl group, an isobutyl group, a sec-butyl group, a tert-butyl group, a pentyl group, and a hexyl group.

The term "C1-C6 alkoxy group" as used herein may be a straight- or branched-chain group, and includes, for example, a methoxy group, an ethoxy group, a propyloxy group, an isopropyloxy group, a butyloxy group, an isobutyloxy group, a sec-butyloxy group, a tert-butyloxy group, a pentyloxy group, and a hexyloxy group.

The term "C1-C6 alkylthio group" as used herein may be a straight- or branched-chain group, and includes, for example, a methylthio group, an ethylthio group, a propylthio group, an isopropylthio group, a butylthio group, an isobutylthio group, a sec-butylthio group, a tert-butylthio group, a pentylthio group, and a hexylthio group.

The term "C1-C3 alkyl group" as used herein includes a methyl group, an ethyl group, a propyl group, and an isopropyl group.

The term "C2-C3 alkenyl group" as used herein includes a vinyl group, a 1-propenyl group, and a 2-propenyl group.

The term "C2-C3 alkynyl group" as used herein includes an ethynyl group, a 1-propynyl group, and a 2-propynyl group.

The term "C3-C4 cycloalkyl group" as used herein includes a cyclopropyl group, and a cyclobutyl group.

The term "C1-C3 alkoxy group" as used herein includes a methoxy group, an ethoxy group, a propyloxy group, and an isopropyloxy group.

The term "C1-C2 alkylthio group" as used herein includes a methylthio group, and an ethylthio group.

The phrase of "can have halogen atom(s) in the alkyl moiety" as used herein means that in the definitions of $R^1$ and $R^2$, the C1-C6 alkyl group, C1-C3 alkyl group, C1-C6 alkoxy group, C1-C3 alkoxy group, C1-C6 alkylthio group, C1-C2 alkylthio group, and C3-C4 cycloalkyl group can have halogen atom(s).

The C1-C6 alkyl group having halogen atom(s) as used herein includes, for example, a monofluoromethyl group, a difluoromethyl group, a trifluoromethyl group, a monochloromethyl group, a dichloromethyl group, a trichloromethyl group, a dibromomethyl group, a chlorofluoromethyl group, a dichlorofluoromethyl group, a chlorodifluoromethyl group, a 2-fluoroethyl group, a 2,2-difluoroethyl group, a 2,2,2-trifluoroethyl group, a pentafluoroethyl group, a 3-fluoropropyl group, a 2,2-difluoropropyl group, a 3,3,3-trifluoropropyl group, a heptafluoropropyl group, a heptafluoroisopropyl group, a 1-(trifluoromethyl)-2,2,2-trifluoroethyl group, a 3-fluoropropyl group, a 4-fluorobutyl group, and a 5-fluorohexyl group.

The C1-C3 alkyl group having halogen atom(s) as used herein includes, for example, a fluoromethyl group, a difluoromethyl group, a trifluoromethyl group, a chloromethyl group, a dichloromethyl group, a trichloromethyl group, a dibromomethyl group, a chlorofluoromethyl group, a dichlorofluoromethyl group, a chlorodifluoromethyl group, a 2-fluoroethyl group, a 2,2-difluoroethyl group, a 2,2,2-trifluoroethyl group, a 2-chloroethyl group, a 2,2-dichloroethyl group, a 2,2,2-trichloropropyl group, a pentafluoroethyl group, a 3-fluoropropyl group, a 3,3,3,-trifluoropropyl group, a heptafluoropropyl group, a heptafluoroisopropyl group, and a 1-(trifluoromethyl)-2,2,2-trifluoroethyl group, and the others.

The C1-C6 alkoxy group having halogen atom(s) as used herein includes, for example, a fluoromethoxy group, a difluoromethoxy group, a trifluoromethoxy group, a chloromethoxy group, a dichloromethoxy group, a trichloromethoxy group, a dibromomethoxy group, a chlorofluoromethoxy group, a dichlorofluoromethoxy group, a chlorodifluoromethoxy group, a 2-fluoroethoxy group, a 2,2,-difluoroethoxy group, a 2,2,2-trifluoroethoxy group, a 2-chloroethoxy group, a 2,2-dichloroethoxy group, a 2,2,2-trichloroethoxy group, a pentafluoroethoxy group, a 3-fluoropropyloxy group, a 3,3,3-trifluoropropyloxy group, a heptafluoropropyloxy group, a heptafluoroisopropyloxy group, a 1-(trifluoromethyl)-2,2,2-trifluoroethyloxy group, a 3-fluoropropyloxy group, a 4-fluorobutyloxy group, and a 5-fluorohexyloxy group and the others.

The C1-C3 alkoxy group having halogen atom(s) includes, for example, a fluoromethoxy group, a difluoromethoxy group, a trifluoromethoxy group, a chloromethoxy group, a dichloromethoxy group, a trichloromethoxy group, a dibromomethoxy group, a chlorofluoromethoxy group, a dichlorofluoromethoxy group, a chlorodifluoromethoxy group, a 2-fluoroethoxy group, a 2,2-difluoroethoxy group, a 2,2,2-trifluoroethoxy group, a 2-chloroethoxy group, a 2,2-dichloroethoxy group, a 2,2,2-trichloroethoxy group, a pentafluoroethoxy group, a 3-fluoropropyloxy group, a 3,3,3-trifluoropropyloxy group, a heptafluoropropyloxy group, a heptafluoroisopropyloxy group, a 1-(trifluoromethyl)-2,2,2-trifluoroethyloxy group, and a 3-fluoropropyloxy group, and the others.

The C1-C6 alkylthio group having halogen atom(s) includes, for example, a monofluoromethylthio group, a difluoromethylthio group, a trifluoromethylthio group, a monochloromethylthio group, a dichloromethylthio group, a trichloromethylthio group, a dibromomethylthio group, a chlorofluoromethylthio group, a dichlorofluoromethylthio group, a chlorodifluoromethylthio group, a 2-fluoroethylthio group, a 2,2-difluoroethylthio group, a 2,2,2-trifluoroethylthio group, a pentafluoroethylthio group, a 3-fluoropropylthio group, a 2,2-difluoropropylthio group, a 3,3,3-trifluoropropylthio group, a heptafluoropropylthio group, a heptafluoroisopropylthio group, a 1-(trifluoromethyl)-2,2,2-trifluoroethylthio group, a 3-fluoropropylthio group, a 4-fluorobutylthio group, and a 5-fluorohexylthio group, and the others.

The C1-C2 alkylthio group having halogen atom(s) includes, for example, a monofluoromethylthio group, a difluoromethylthio group, a trifluoromethylthio group, a monochloromethylthio group, a dichloromethylthio group, a trichloromethylthio group, a dibromomethylthio group, a chlorofluoromethylthio group, a dichlorofluoromethylthio group, a chlorodifluoromethylthio group, a 2-fluoroethylthio group, a 2,2-difluoroethylthio group, a 2,2,2-trifluoroethylthio group, and a pentafluoroethylthio group, and the others.

The C3-C4 cycloalkyl group having halogen atom(s) includes, for example, a 2-fluorocyclopropyl group, a 2,2-difluorocyclopropyl group, a 2-chloro-2-fluorocyclopropyl group, a 2,2-dichlorocyclopropyl group, a 2,2-dibromocyclopropyl group, and a 2,2,3,3-tetrafluorocyclobutyl group, and the others.

First, a process for preparing the present tetrazolinone compound is explained.

The present tetrazolinone compound may be prepared, for example, according to the below-mentioned processes.

(Process A)

The present tetrazolinone compound may be prepared by reacting a compound represented by a formula (2) (hereinafter referred to as Compound (2)) with a compound represented by a formula (3) (hereinafter referred to as Compound (3)) in the presence of a base.

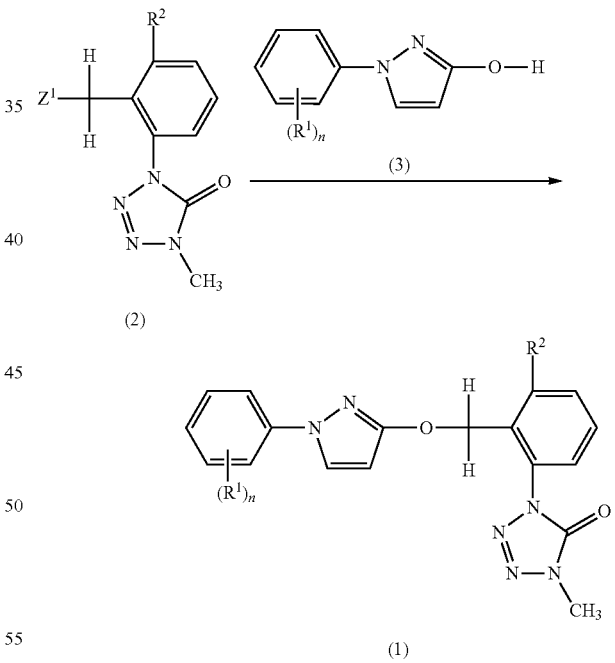

[wherein, n, and $R^1$ and $R^2$ are the same as defined above, respectively, and $Z^1$ represents a leaving group such as a chlorine atom, a bromine atom, or an iodine atom]

The reaction is usually carried out in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate, and methyl acetate; sulfoxides such as dimethyl sulfoxide; ketones such as acetone, methyl ethyl ketone, and methyl isobutyl ketone; nitriles such as acetonitrile, and propionitrile; water; and mixed solvents thereof.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal bicarbonates such as lithium bicarbonate, sodium bicarbonate, potassium bicarbonate, and cesium bicarbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide, and potassium tert-butoxide.

In the reaction, Compound (3) is used usually within a range of 1 to 10 molar ratio(s), and the base is used usually within a range of 0.5 to 5 molar ratio(s), as opposed to 1 mole of Compound (2).

The reaction temperature is usually within a range of −20 to 150° C. The reaction period of the reaction is usually within a range of 0.1 to 24 hours.

If necessary, sodium iodide, tetrabutylammonium iodide and the others may be added to the reaction, and these compounds are used usually within a range of 0.001 to 1.2 molar ratio(s) as opposed to 1 mole of Compound (2).

When the reaction is completed, the reaction mixtures are extracted with organic solvent(s), and the resulting organic layers are worked up (for example, drying and concentration) to isolate the present tetrazolinone compound. The isolated tetrazolinone compound may be further purified, for example, by chromatography and recrystallization.

(Process B)

The present tetrazolinone compound may be prepared by reacting a compound represented by a formula (4) (hereinafter referred to as Compound (4)) with a compound represented by a formula (5) (hereinafter referred to as Compound (5)) in the presence of a catalyst and a base.

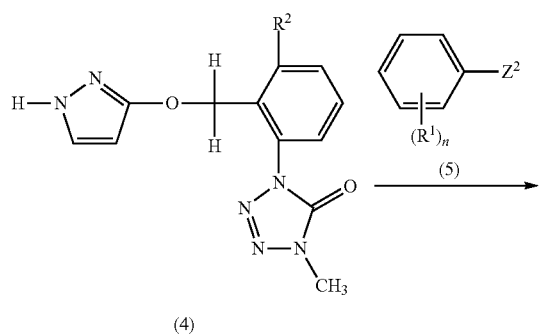

(4)

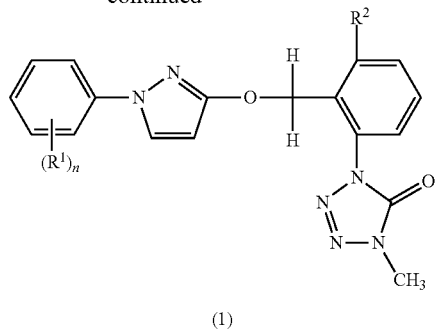

(1)

[wherein, n, $R^1$, $R^2$ are the same as defined above, respectively, and $Z^2$ represents a leaving group such as a chlorine atom, a bromine atom, an iodine atom, a methanesulfonyloxy group, a trifluoromethanesulfonyloxy group, and a p-toluenesulfonyloxy group, a $B(OH)_2$, an alkoxyboryl group, or a trifluoroborate $(BF_3^-K^+)$.]

The reaction is usually carried out in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate, and methyl acetate; sulfoxides such as dimethyl sulfoxide; ketones such as acetone, methyl ethyl ketone, and methyl isobutyl ketone; nitriles such as acetonitrile, and propionitrile; and mixed solvents thereof.

Compound (5) to be used in the reaction can be usually used as a commercially available product. Specific examples include chlorobenzene, bromobenzene, iodobenzene, paradichlorobenzene, 4-chlorobromobenzene, 4-chloroidobenzene 4-bromoiodobenzene, phenylboronic acid, 4-fluorophenylboronic acid, 4-chlorophenylboronic acid, 4-methylphenylboronic acid, and 4-methoxyphenylboronic acid.

Examples of the catalyst to be used in the reaction include copper(I) iodide, copper(II) acetate, palladium(II) acetate, dichlorobis(triphenylphosphine)palladium, tetrakistriphenylphosphine palladium(0), palladium(II) acetate/triscyclohexylphosphine, bis(diphenylphoshine ferrocenyl)palladium(II) dichloride, 1,3-bis(2,6-diisopropylphenyl)imidazol-2-ylidene (1,4-naphthoquinone)palladium dimer, aryl(chloro)(1,3-dimesityl-1,3-dihydro-2H-imidazol-2-ylidene)palladium, or palladium(II) acetate/dicyclohexyl(2',4',6'-triisopropyibiphenyl-2-yl)phosphine, and tris(dibenzylideneacetone)dipalladium.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal bicarbonates such as lithium bicarbonate, sodium bicarbonate, potassium bicarbonate, and cesium bicarbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, Compound (5) is used usually within a range of 1 to 10 molar ratio(s), and the catalyst is used usually within a range of 0.001 to 5 molar ratio(s), and the base is used usually within a range of 0.5 to 10 molar ratio(s), as opposed to 1 mole of Compound (4).

If necessary, a ligand such as 1,10-phenanthroline, tetramethylenediamine and the others may be added to the reaction, and these compounds are used usually within a range of 0.001 to 5 molar ratio(s) as opposed to 1 mole of Compound (4).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound. The isolated tetrazolinone compound may be further purified, for example, by chromatography and recrystallization.

(Process C)

The present tetrazolinone compound may be prepared by coupling a compound represented by a formula (6) (hereinafter referred as to Compound (6)) (which may be prepared according to the similar method to Process A) with a compound represented by a formula (7) (hereinafter referred as to Compound (7)) in the presence of a base and a catalyst.

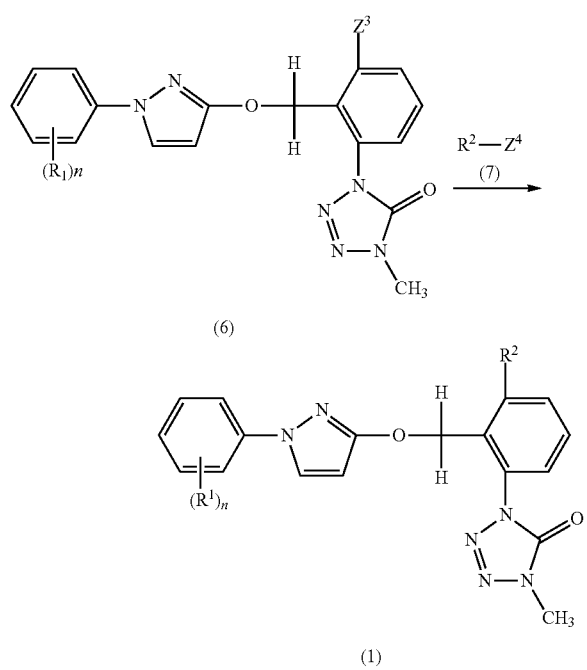

[wherein n, $R^1$ and $R^2$ are the same as defined above, respectively, $Z^3$ represents a chlorine atom, a bromine atom, an iodine atom, or a trifluoromethanesulfonyloxy group, and $Z^4$ represents a B(OH)$_2$, an alkoxyboryl group, or a trifluoroborate (BF$_3^-$K$^+$).]

The reaction is usually carried out in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate, and methyl acetate; sulfoxides such as dimethyl sulfoxide; ketones such as acetone, methyl ethyl ketone, and methyl isobutyl ketone; nitriles such as acetonitrile, and propionitrile; alcohols such as methanol, ethanol, propanol, and butanol; water, and mixed solvents thereof.

Organoboron compound (7) to be used in the reaction may be used as a commercially available compound, or may be prepared according to a method described in a review article of N. Miyaura and A. Suzuki, Chem. Rev. 1995, 95, 2457 and the others. The organoboron compound (7) to be used in the reaction can be prepared, for example, by reacting an iodo compound for $R^2$ ($R^2$-I) or a bromo compound for $R^2$ ($R^2$-Br) with an alkyl lithium (such as butyl lithium), followed by reacting the resulting mixtures with boronate esters to obtain boronate ester derivatives. Also, the boronate ester derivatives obtained in the above-mentioned reaction can be hydrolyzed as needed to the corresponding boronic acid derivatives. Further, according to a method described in a review article of Molander et al. Acc. Chem. Res. 2007, 40, 275 and the like, the above-mentioned boronate ester derivatives can be fluorinated with potassium bifluoride and the like to obtain the trifluoroborate salts BF$_3^-$K$^+$.

Examples of the catalyst to be used in the reaction include palladium(II) acetate, dichlorobis(tripheny phosphine)palladium, tetrakistriphenylphosphine palladium(0), palladium (II) acetate/tricyclohexylphosphine, bis(diphenylphoshine ferrocenyl)palladium(II) dichloride, 1,3-bis(2,6-diisopropylphenyl)imidazol-2-ylidene (1,4-naphthoquinone)palladium dimer, aryl(chloro) (1,3-dimethyl-1,3-dihydro-2H-imidazol-2-ylidene)palladium or palladium(II) acetate/dicyclohexyl (2',4',6'-triisopropylbiphenyl-2-yl)phosphine, and tris (dibenzylideneacetone)dipalladium and the others.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene; alkali metal carbonates such as lithium carbonate, sodium carbonate, potassium carbonate, and cesium carbonate; alkali metal bicarbonates such as lithium bicarbonate, sodium bicarbonate, potassium bicarbonate, and cesium bicarbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; alkali metal phosphates such as tripotassium phosphate; and alkali metal alkoxides such as sodium methoxide, sodium ethoxide, sodium tert-butoxide, and potassium tert-butoxide.

In the reaction, Compound (7) is used usually within a range of 1 to 10 molar ratio(s), and the base is used usually within a range of 1 to 10 molar ratio(s), and the catalyst is used usually within a range of 0.0001 to 1 molar ratio(s), as opposed to 1 mole of Compound (6).

The reaction temperature is usually within a range of 0 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate the present tetrazolinone compound. The isolated tetrazolinone compound may be further purified, for example, by chromatography and recrystallization.

Next, a method for preparing a synthetic intermediate compound of the present tetrazolinone compound is explained in detail.

(Reference Process A)

The compound represented by a formula (9) (hereinafter referred to as Compound (9)) may be prepared by reacting the Compound (2) with a compound represented by a formula (8) (hereinafter referred to as Compound (8)) in the presence of a base.

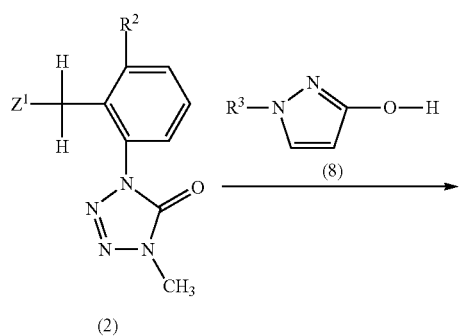

(2)

(8)

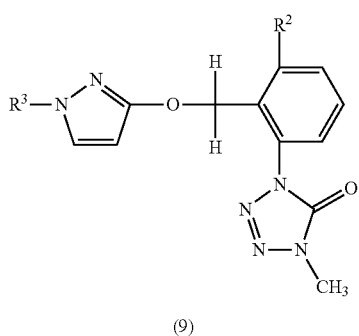

(9)

[wherein, $R^2$ and $Z^1$ are the same as defined above, respectively, and $R^3$ represents a protecting group such as an acetyl, group, a formyl group, a benzoyl group, a methoxycarbonyl group, an ethoxycarbonyl group, a benzyloxycarbonyl group, and a tert-butoxycarbonyl group.]

The reaction can be carried out according to the above-mentioned process A.

(Reference Process B)

The compound represented by formula (4) may be prepared by treating the Compound (9) with a deprotecting agent.

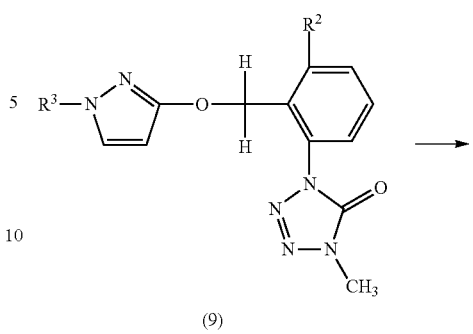

(9)

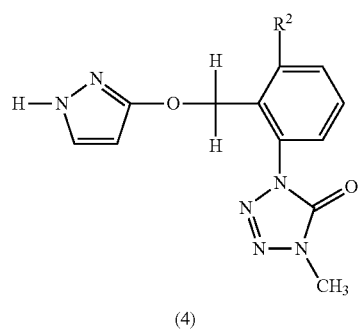

(4)

[wherein, $R^2$ and $R^3$ are the same as defined above, respectively.]

The reaction is usually carried out in a solvent.

Examples of the solvent to be used in the reaction include ethers such as diethyl ether, tetrahydrofuran, 1,4-dioxane, ethyleneglycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile, and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; water; and mixed solvents thereof.

The deprotecting agent to be used in the reaction may be used as a base or an acid. Examples of the base include organic bases such as triethylamine, pyridine, N-methylmorpholine, N-methylpiperidine, 4-dimethylaminopyridine, diisopropylethylamine, lutidine, collidine, diazabicycloundecene, and diazabicyclononene, piperidine; alkali metal hydroxides such as lithium hydroxide, sodium hydroxide, potassium hydroxide, and cesium hydroxide; alkali metal alkoxides such as sodium methoxide, sodium ethoxide, sodium tert-butoxide, and potassium tert-butoxide. Examples of the acid include trifluoroacetic acid, hydrochloric acid, and sulfuric acid.

In the reaction, the deprotecting agent is used usually within a range of 1 to 100 molar ratio(s) as opposed to 1 mole of Compound (9).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (4). The isolated Compound (4)

may be further purified, for example, by distillation, chromatography and recrystallization.

(Reference Process C)

The compound represented by a formula (11) (hereinafter referred to Compound (11)) may be prepared by reacting a compound represented by a formula (10) (hereinafter referred to as Compound (10)) with an azidation agent.

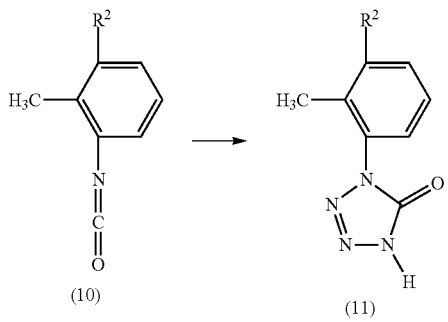

[wherein,
$R^2$ is the same as defined above.]

The reaction is usually carried out in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate, and methyl acetate; sulfoxides such as dimethyl sulfoxide; ketones such as acetone, methyl ethyl ketone, methyl isobutyl ketone; nitriles such as acetonitrile, and propionitrile; and mixed solvents thereof.

Examples of the azidation agent to be used in the reaction include inorganic azides such as sodium azide, barium azide, and lithium azide; and organic azides such as trimethylsilyl azide and diphenylphosphoryl azide.

In the reaction, the azidation agent is used usually within a range of 1 to 10 molar ratio(s) as opposed to mole of Compound (10).

The reaction temperature is usually within a range of −20 to 150° C. The reaction period of the reaction is usually within a range of 0.1 to 24 hours.

If necessary, a Lewis acid such as aluminium chloride and zinc chloride may be added to the reaction, and these compounds are used usually within a range of 0.05 to 5 molar ratio(s) as opposed to 1 mole of Compound (10).

When the reaction is completed, the reaction mixtures are extracted with organic solvent(s), and the resulting organic layers are worked up (for example, drying and concentration) to isolate Compound (11). The isolated Compound (11) may be further purified, for example, by chromatography and recrystallization.

(Reference Process D)

The compound represented by a formula (13) (hereinafter referred to as Compound (13)) may be prepared by reacting the Compound (11) with a compound represented by a formula (12) (hereinafter referred to as Compound (12)) in the presence of a base.

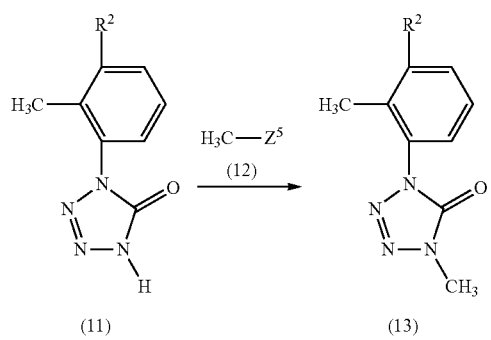

[wherein,
$R^2$ is the same as defined above, and $Z^5$ represents a leaving group such as a bromine atom, an iodine atom, a methanesulfonyloxy group, a trifluoromethanesulfonyloxy group, and a p-toluenesulfonyloxy group.]

The reaction is usually carried out in a solvent.

Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, and chlorobenzene; acid amides such as N,N-dimethylformamide, 1,3-dimethyl-2-imidazolidinone, and N-methylpyrrolidone; esters such as ethyl acetate, and methyl acetate; sulfoxides such as dimethyl sulfoxide; ketones such as acetone, methyl ethyl ketone, and methyl isobutyl ketone; nitriles such as acetonitrile, and propionitrile; water; and mixed solvents thereof.

Compound (12) to be used in the reaction can be usually used as a commercially available product. Specific examples include alkyl halides such as methyl bromide, and methyl iodide; dialkyl sulfates such as dimethyl sulfate; alkyl or aryl sulfates such as methyl p-toluenesulfonate, and methyl methanesulfonate.

Examples of the base to be used in the reaction include organic bases such as triethylamine, pyridine, N-methylmorpholine, N-methylpiperidine, 4-dimethylaminopyridine, diisopropylethylamine, lutidine, collidine, diazabicycloundecene, diazabicyclononene; alkali metal carbonates such as lithium carbonate, sodium carbonate, potassium carbonate, and cesium carbonate; alkali metal bicarbonates such as lithium bicarbonate, sodium bicarbonate, potassium bicarbonate, and cesium bicarbonate; alkali metal hydroxides such as lithium hydroxide, sodium hydroxide, potassium hydroxide, and cesium hydroxide; alkali metal halides such as sodium fluoride, potassium fluoride, and cesium fluoride; alkali metal hydrides such as lithium hydride, sodium hydride, and potassium hydride; and alkali metal alkoxides such as sodium tert-butoxide, and potassium tert-butoxide.

In the reaction, Compound (12) is used usually within a range of 1 to 10 molar ratio(s), and the base is used usually within a range of 0.5 to 10 molar ratios, as opposed to 1 mole of Compound (11).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (13). The isolated Compound (13) may be further purified, for example, by chromatography and recrystallization.
(Reference Process E)
The Compound (2) may be prepared by reacting the Compound (13) with a halogenating agent.

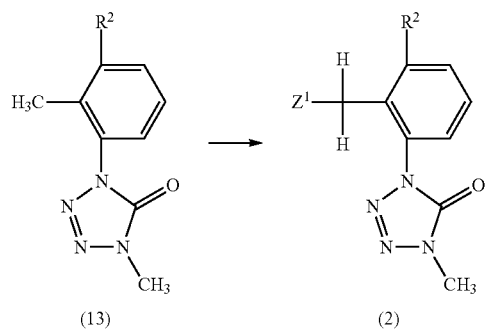

(13)    (2)

[wherein,
R² and Z¹ are the same as defined above, respectively.]
The reaction is usually carried out in a solvent.
Examples of the solvent to be used in the reaction include hydrocarbons such as n-heptane, n-hexane, cyclohexane, n-pentane, toluene, and xylene; ethers such as diethyl ether, tetrahydrofuran, 1,4-dioxane, ethyleneglycol dimethyl ether, anisole, methyl tert-butyl ether, and diisopropyl ether; halogenated hydrocarbons such as carbon tetrachloride, chloroform, dichloromethane, 1,2-dichloroethane, tetrachloroethane, fluorobenzene, difluorobenzene, trifluorobenzene, chlorobenzene, dichlorobenzene, trichlorobenzene, α,α,α-trifluorotoluene, and α,α,α-trichlorotoluene; esters such as ethyl acetate, and methyl acetate; ketones such as acetone, methyl ethyl ketone, and methyl isobutyl ketone; nitriles such as acetonitrile, and propionitrile; and mixed solvents thereof.

Examples of the halogenating agent to be used in the reaction include a chlorinating agent, a brominating agent or iodinating agent such as chlorine, bromine, iodine, sulfuryl chloride, N-chlorosuccinimide, N-bromosuccinimide, 1,3-dibromo-5,5-dimethylhydantoin, iodosuccinimide, tert-butyl hypochlorite, N-chloroglutarimide, N-bromoglutarimide, N-chloro-N-cyclohexyl-benzenesulfonamide, and N-bromophthalimide.

A radical initiator may be used in the reaction.
Examples of the radical initiator to be used in the reaction include benzoyl peroxide, azobisisobutyronitrile (AIBN), azobiscyclohexanecarbonitrile, diacylperoxide, dialkyl peroxydicarbonate, tert-alkyl peroxyester, monoperoxy carbonate, di(tert-alkylperoxy)ketal, and ketone peroxide.

In the reaction, the halogenating agent is used usually within a range of 1 to 10 molar ratio(s), and the radical initiator is used usually within a range of 0.01 to 1 molar ratio(s), as opposed to 1 mole of Compound (13).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (2-1). The isolated Compound (2-1) may be further purified, for example, by chromatography and recrystallization.

(Reference Process F)
A compound represented by a formula (15) (hereinafter referred to as Compound (15)) can be prepared by reacting a compound represented by a formula (2-1) wherein R² in a formula (2) represents Z¹ (hereinafter referred to as Compound (2-1)) with a compound represented by a formula (15) (hereinafter referred to as Compound (15)).

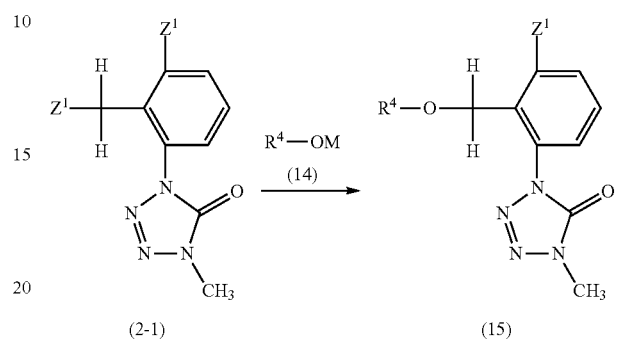

(2-1)    (15)

[wherein,
Z¹ is the same as defined above, R⁴ represents a C1-C12 alkyl group or a phenyl group, and M represents sodium, potassium or lithium.]

The reaction is usually carried out in a solvent.
Examples of the solvent to be used in the reaction include ethers such as diethyl ether, tetrahydrofuran, 1,4-dioxane, ethyleneglycol dimethyl ether, anisole, methyl tert-butyl ether, and diisopropyl ether; hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; nitriles such as acetonitrile, and propionitrile; acid amides such as N,N-dimethylformamide, 1,3-dimethyl-2-imidazolidinone, and N-methylpyrrolidone; sulfoxides such as dimethyl sulfoxide; ketones such as acetone, methyl ethyl ketone, and methyl isobutyl ketone; alcohols such as methanol, ethanol, propanol, and butanol; and mixed solvents thereof.

Examples of Compound (14) include sodium methoxide, sodium ethoxide, sodium n-propoxide, sodium n-butoxide, sodium isopropoxide, sodium sec-butoxide, sodium tert-butoxide, potassium methoxide, potassium ethoxide, potassium n-propoxide, potassium n-butoxide, potassium isopropoxide, potassium sec-butoxide, potassium tert-butoxide, potassium methoxide, and sodium phenoxide.

In the reaction, Compound (14) is used usually within a range of 1 to 10 molar ratio(s) as opposed to 1 mole of Compound (2-2).

The reaction temperature is usually within a range of −20 to 150° C. The reaction period of the reaction is usually within a range of 0.1 to 24 hours.

When the reaction is completed, the reaction mixtures are extracted with organic solvent(s), and the resulting organic layers are worked up (for example, drying and concentration) to isolate Compound (15). The isolated Compound (15) may be further purified, for example, by distillation, chromatography and recrystallization.

(Reference Process G)
A compound represented by a formula (16) (hereinafter referred to as Compound (16)) can be prepared by reacting Compound (15) and Compound (7) in the presence of a base.

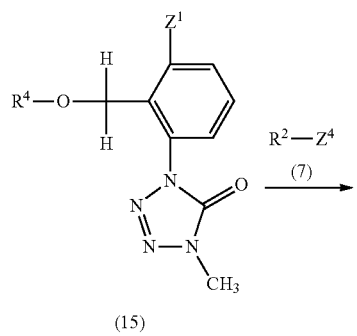

(15)

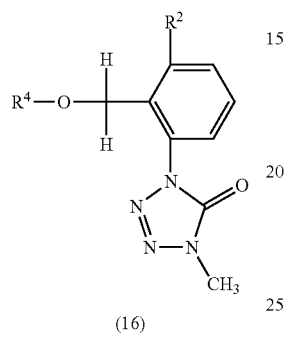

(16)

[wherein,

R², R⁴, Z⁴ and Z¹ are the same as defined above, respectively.]

The reaction can be carried out according to the above-mentioned Process C.

(Reference Process H)

The Compound (2) can be also prepared by reacting Compound (16) and a halogenating agent.

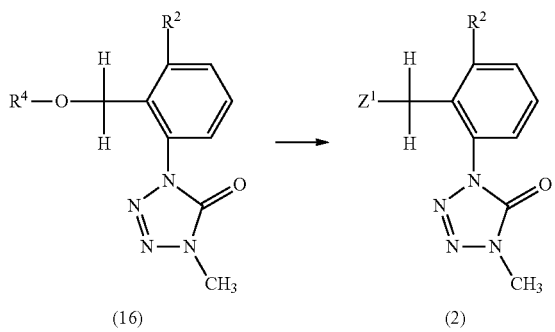

[wherein,

R², R⁴ and Z¹ are the same as defined above, respectively.]

The reaction is usually carried out in a solvent.

Examples of the solvent to be used in the reaction include hydrocarbons such as n-heptane, n-hexane, cyclohexane, n-pentane, toluene, and xylene; halogenated hydrocarbons such as carbon tetrachloride, chloroform, dichloromethane, 1,2-dichloroethane, tetrachloroethane, and chlorobenzene; ketones such as acetone, methyl ethyl ketone, and methyl isobutyl ketone; nitriles such as acetonitrile, and propionitrile; organic acids such as formic acid, acetic acid, and trifluoroacetic acid; water; and mixed solvents thereof Examples of the halogenating agent include hydrochloric acid, hydrobromic acid, and hydroiodic acid.

In the reaction, the halogenating agent is used usually within a range of 1 or more molar ratio(s) as opposed to 1 mole of Compound (16).

The reaction temperature is usually within a range of −20 to 150° C. The reaction period of the reaction is usually within a range of 0.1 to 24 hours When the reaction is completed, the reaction mixtures are extracted with organic solvent(s), and the resulting organic layers are worked up (for example, drying and concentration) to isolate Compound (2-1). The isolated Compound (2-1) may be further purified, for example, by distillation, chromatography and recrystallization.

The present carboxamide compounds are all known compounds, and they are described in "THE PESTICIDE MANUAL -16th EDITION (published by BCPC) ISBN 9781901396867", WO 2011/162397, WO 2006/016708, or WO 2007/072999. These compounds may be obtained from commercially available formulations or may be prepared according to known methods.

Examples of an embodiment of N-(1,1,3-trimethylindan-4-yl)-1-methyl-3-difluoromethylpyrazole-4-carboxylic acid amide as described herein include a compound represented by a formula (a1):

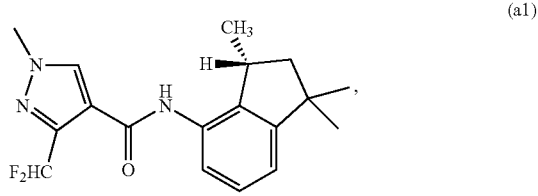

(a1)

and/or a compound represented by formula (a2):

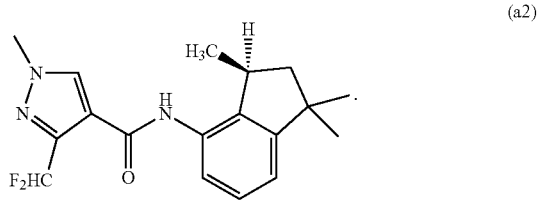

(a2)

The present carboxamide compounds are shown in [Table 1] below.

TABLE 1

| Compound | Present carboxamide compound |
| --- | --- |
| Compound I | bixafen |
| Compound II | benzovindiflupyr |
| Compound III | fluxapyroxad |
| Compound IV | boscalid |
| Compound V | compound represented by formula (a1) |
| Compound VI | compound represented by formula (b) |
| Compound VII | isofetamid or N-[1,1-dimethyl-2-(4-isopropoxy-o-tolyl)-2-oxoethyl]-3-methylthiophene-2-carboxamide |
| Compound VIII | isopyrazam |
| Compound IX | penthiopyrad |
| Compound X | fluopyram |
| Compound XI | sedaxane |
| Compound XII | penflufen |
| Compound XIII | flutolanil |
| Compound XIV | mepronil |
| Compound XV | carboxin |

TABLE 1-continued

| Compound | Present carboxamide compound |
|---|---|
| Compound XVI | thifluzamide |
| Compound XVII | furametpyr |
| Compound XVIII | compound represented by formula (a2) |

In the composition of the present invention, a weight ratio of the present tetrazolinone compound to the present carboxamide compound includes, for example, the present tetrazolinone compound/the present carboxamide compound=0.01/1 to 500/1, 0.1/1 to 10/1, and 0.1/1 to 3/1, and preferably 0.3/1 to 3/1.

The composition of the present invention may be a mixture as itself of the present tetrazolinone compound and the present carboxamide compound, and is usually prepared by mixing the present tetrazolinone compound, the present carboxamide compound and an inert carrier, optionally adding a surfactant and other auxiliaries for formulation.

The composition of the present invention may be formulated into an oil solution, an emulsifiable concentrate, a flowable formulation, a wettable powder, a water dispersible granule, a dust, or a granule. The thus formulations can be used directly as a plant disease control agent, or used after the addition of other inert ingredients.

The total amount of the present tetrazolinone compound and the present carboxamide compound in the composition of the present invention is usually within a range from 0.1% to 99% by weight, preferably from 0.2% to 90% by weight, and more preferably from 1% to 80% by weight.

Examples of the solid carrier to be used in the formulation include clays (for example, kaolin, diatomaceous earth, synthetic hydrated silicon dioxide, Fubasami clay, bentonite and acid clay), talcs or the other inorganic minerals (for example, sericite, quartz powder, sulfur powder, activated charcoal, calcium carbonate and hydrated silica) in the form of fine powders or particulates, and examples of the liquid carrier include water, alcohols (for example, methanol and ethanol), ketones (for example, acetone and methyl ethyl ketone), aromatic hydrocarbons (for example, benzene, toluene, xylene, ethylbenzene and methyl naphthalene), aliphatic hydrocarbons (for example, n-hexane, cyclohexane and kerosene), esters (for example, ethyl acetate and butyl acetate), nitriles (for example, acetonitrile and isobutyronitrile), ethers (for example, dioxane and diisopropylether), acid amides (for example, DMF and dimethylacetamide), halogenated hydrocarbons (for example, dichloroethane, trichloro ethylene and carbon tetrachloride) and the others.

Examples of the surfactants include alkyl sulfates, alkyl sulfonates, alkyl aryl sulfonates, alkyl aryl ethers and polyoxyethylenated compounds thereof, polyethylene glycol ethers, polyol esters and sugar alcohol derivatives.

Examples of other auxiliary agents for formulation include a sticker, a dispersant and a stabilizer, and specific examples include casein, gelatin, polysaccharides (for example, starch, gum arabic, cellulose derivatives and alginic acid), lignin derivatives, bentonite, sugars, water-soluble synthetic polymers (for example, polyvinyl alcohol, polyvinyl pyrrolidone and polyacrylic acids), PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, fatty acids or fatty acid esters thereof and the others.

The composition of the present invention may be also formulated by formulating each of the present tetrazolinone compound and the present carboxamide compound according the above-mentioned method and if necessary, diluting it with water to obtain a formulation containing the present tetrazolinone compound or diluted solutions containing the same, or a formulation containing the present carboxamide compound or diluted solutions containing the same, respectively, followed by mixing the resulting formulations or diluted solutions to each other.

The composition of the present invention can be used to protect plants from plant diseases.

The control method of the present invention can control plant diseases by applying the composition of the present invention to plants or soil for cultivating plants, alternatively by applying the present tetrazolinone compound or the present carboxamide compound separately to plants or soil for cultivating plants.

The method for applying the composition of the present invention is not particularly limited, as far as the applying form is a form by which the present compound may be applied substantially, and includes, for example, an application to plants such as a foliar application; an application to area for cultivating plants such as a submerged treatment; and an application to seed such as seed disinfection.

The application dose of the composition of the present invention varies depending on weather conditions, dosage forms, timing of application, methods of application, areas to be applied, target diseases, target crops and the others, and is in the range of usually from 1 to 500 g, and preferably from 2 to 200 g per 1,000 $m^2$ of the area to be applied. The emulsifiable concentrate, the wettable powder or the suspension concentrate etc., is usually applied by diluting it with water. In this case, the concentration of the composition of the present invention after dilution is in the range of usually 0.0005 to 2% by weight, and preferably 0.005 to 1% by weight, and the dust formulation or the granular formulation etc., is usually applied as itself without diluting it. In the application to seeds, the amount of the composition of the present invention is in the range of usually from 0.001 to 100 g, and preferably from 0.01 to 50 g per 1 kg of the seeds.

Examples of the place where the plant diseases grow include paddy fields, fields, tea gardens, orchards, non-agricultural lands, houses, nursery trays, nursery boxes, nursery soils and nursery bed.

The composition of the present invention can be used as agent for controlling plant disease in agricultural lands such as fields, paddy fields, lawns, and orchards. The composition of the present invention can control diseases occurred in the agricultural lands or the others for cultivating the following "plant" and the others.

Crops:
corn, rice, wheat, barley, rye, oat, sorghum, cotton, soybean, peanut, buckwheat, beet, rapeseed, sunflower, sugar cane, tobacco, and the others;

Vegetables:
solanaceous vegetables (for example, eggplant, tomato, pimento, pepper and potato),
cucurbitaceous vegetables (for example, cucumber, pumpkin, zucchini, water melon and melon),
cruciferous vegetables (for example, Japanese radish, white turnip, horseradish, kohlrabi, Chinese cabbage, cabbage, leaf mustard, broccoli, cauliflower),
asteraceous vegetables (for example, burdock, crown daisy, artichoke and lettuce),
liliaceous vegetables (for example, green onion, onion, garlic and asparagus),
ammiaceous vegetables (for example, carrot, parsley, celery and parsnip), chenopodiaceous vegetables (for example, spinach and Swiss chard),
lamiaceous vegetables (for example, Perilla frutescens, mint and basil),
strawberry, sweet potato, Dioscorea japonica, colocasia and the others;
Flowers:
Ornamental foliage plants:
Fruits:
pomaceous fruits (for example, apple, pear, Japanese pear, Chinese quince and quince),
stone fruits (for example, peach, plum, nectarine, Prunus mume, cherry fruit, apricot and prune),
citrus fruits (for example, Citrus unshiu, orange, lemon, lime and grapefruit),
nuts (for example, chestnut, walnuts, hazelnuts, almond, pistachio, cashew nuts and macadamia nuts),
berry fruits (for example, blueberry, cranberry, blackberry and raspberry),
grapes, kaki persimmon, olive, Japanese plum, banana, coffee, date palm, coconuts, and the others;
Trees other than fruit trees:
tea, mulberry, flowering plant,
roadside trees (for example, ash, birch, dogwood, *Eucalyptus, Ginkgo biloba*, lilac, maple, *Quercus*, poplar, Judas tree, *Liquidambar formosana*, plane tree, *zelkova*, Japanese arborvitae, fir wood, hemlock, *juniper, Pinus, Picea,* and *Taxus cuspidate*); and the others.

The above-mentioned "plant" includes genetically modified crops.

The pests on which the composition of the present invention has a control efficacy include plant pathogens such as filamentous fungus, and specifically include the following examples, but are not limited thereto.

Rice diseases: blast (*Magnaporthe grisea*), brown spot (*Cochliobolus miyabeanus*), sheath blight (*Rhizoctonia solani*), and bakanae disease (*Gibberella fujikuroi*);

Wheat diseases: powdery mildew (*Erysiphe graminis*), fusarium blight (*Fusarium gaminearum*, F. avenaceum, F. culmorum, Microdochium nivale), rust (*Puccinia striiformis, P. graminis, P. recondita*), snow mould (*Micronectriella nivale*), typhulasnow blight (*Typhula* sp.), loose smut (*Ustilago tritici*), stinking smut (*Tilletia caries*), eyespot (*Pseudocercosporella herpotrichoides*), leaf blotch (*Mycosphaerella graminicola*), glume blotch (*Stagonospora nodorum*), tan spot (*Pyrenophora tritici-repentis*);

Barly diseases: powdery mildew (*Erysiphe graminis*), fusarium blight (Fusarium gaminearum, F. avenaceum, F. culmorum, Microdochium nivale), rust (*Puccinia striiformis, P. graminis, P. hordei*), loose smut (*Ustilago nuda*), scald (*Rhynchosporium secalis*), net blotch (*Pyrenophora teres*), spot blotch (*Cochliobolus sativus*), leaf stripe (*Pyrenophora graminea*), and rhizoctonia seeding blight (*Rhizoctonia solani*);

Corn diseases: smut (*Ustilago maydis*), southern leaf blight (*Cochliobolus heterostrophus*), Zonate leaf spot (*Gloeocercospora sorghi*), southern rust (*Puccinia polysora*), gray leaf spot (*Cercospora zeae-maydis*), and rhizoctonia seeding blight (*Rhizoctonia solani*);

Citrus diseases: melanose (*Diaporthe citri*), scab (*Elsinoe fawcetti*), fruit rot (*Penicillium digitatum, P. italicum*); Phytophthora diseases (*Phytophthora parasitica, Phytophthora citrophthora*);

Apple diseases: blossom blight (*Monilinia mali*), canker (*Valsa ceratosperma*), powdery mildew (*Podosphaera leucotricha*), alternaria leaf spot (*Alternaria alternata* apple pathotype), scab (*Venturia inaequalis*), bitter rot (*Colletotrichum acutatum*), and crown rot (*Phytophtora cactorum*);

Pear diseases: scab (*Venturia nashicola, V. pirina*), black spot (*Alternaria alternata* Japanese pear pathotype), rust (*Gymnosporangium haraeanum*), and phytophthora fruit rot (*Phytophtora cactorum*);

Peach diseases: brown rot (*Monilinia fructicola*), scab (*Cladosporium carpophilum*) and Phomopsis rot (*Phomopsis* sp.);

Grapes diseases: anthracnose (*Elsinoe ampelina*), ripe rot (*Glomerella cingulata*), powdery mildew (*Uncinula necator*), rust (*Phakopsora ampelopsidis*), black rot (*Guignardia bidwellii*), and downy mildew (*Plasmopara viticola*);

Diseases of Japanese persimmon: anthracnose (*Gloeosporium kaki*), and leaf spot (*Cercospora kaki, Mycosphaerella nawae*);

Diseases of gourd family: anthracnose (*Colletotrichum lagenarium*), powdery mildew (*Sphaerotheca fuliginea*), vine blight (*Mycosphaerella melonis*), fusarium wilt (*Fusarium oxysporum*), downy mildew (*Pseudoperonospora cubensis*), phytophthora rot (*Phytophthora* sp.), and damping-off (*Pythium* sp.);

Tomato diseases: early blight (*Alternaria solani*), leaf mold (*Cladosporium fulvum*), and late blight (*Phytophthora infestans*);

Eggplant disease: brown spot (*Phomopsis vexans*), and powdery mildew (*Erysiphe cichoracearum*);

Diseases of Cruciferous Vegetables: alternaria leaf spot (*Alternaria japonica*), white spot (*Cercosporella brassicae*), clubroot (*Plasmodiophora brassicae*), and downy mildew (*Peronospora parasitica*);

Welsh onion diseases: rust (*Puccinia allii*) and downy mildew (*Peronospora destructor*);

Soybean diseases: purple stain (*Cercospora kikuchii*), sphaceloma scad (*Elsinoe glycines*), pod and stem blight (*Diaporthe phaseolorum* var. *sojae*), septoria brown spot (*Septoria glycines*), frog eye leaf spot (*Cercospora sojina*), rust (*phakopsora pachyrhizi*), phytophthora root and stem rot (*Phytophthora sojae*), rhizoctonia aerial blight (*Rhizoctonia solani*), target spot (*Corynespora cassiicola*), and sclerotinia stem rot (*Sclerotinia sclerotiorum*);

Kindney bean diseases: anthracnose (*Colletotrichum lindemthianum*);

Peanut diseases: early leaf spot (*Cercospora personata*), late leaf spot (*Cercospora arachidicola*), and southern blight (*Sclerotium rolfsii*);

Garden pea diseases: powdery mildew (Erysiphe pisi);

Potato diseases: early blight (*Alternaria solani*), late blight (*Phytophthora infestans*), Pink rot (*Phytophthora Erythroseptica*), and powdery scab (*Spongospora subterranean* f. sp. *subterranea*);

Strawberry diseases: powdery mildew (*Sphaerotheca humuli*), and anthracnose (*Glomerella cingulata*);

Tea diseases: net blister blight (*Exobasidium reticulatum*), white scab (*Elsinoe leucospila*), gray blight (*Pestalotiopsis* sp.) and anthracnose (*Colletotrichum theae-sinensis*);

Tabacco diseases: brown spot (*Alternaria longipes*), powdery mildew (*Erysiphe cichoracearum*), anthracnose (*Colletotrichum tabacum*), downy mildew (*Peronospora tabacina*), and black shank (*Phytophthora nicotianae*);

Rapeseed diseases: sclerotinia rot (*Sclerotinia sclerotiorum*), and rhizoctonia seeding blight (*Rhizoctonia solani*);

Cotton diseases: rhizoctonia seeding blight (*Rhizoctonia solani*);

Sugar beet diseases: cercospora leaf spot (*Cercospora beticola*), leaf blight (*Thanatephorus cucumeris*), root rot (*Thanatephorus cucumeris*), and aphanomyces root rot (*Aphanomyces cochlioides*);

Rose diseases: black spot (*Diplocarpon rosae*), powdery mildew (*Sphaerotheca pannosa*), and downy mildew (*Peronospora sparsa*);

Diseases of Chrysanthemum: downy mildew (*Bremia lactucae*), leaf blight (*Septoria chrysanthemi-indici*), and white rust (*Puccinia horiana*);

Various crops diseases: diseases caused by *Pythium* spp. (*Pythium aphanidermatum, Pythium debarianum, Pythium irregulare*, and *Pythium ultimum*), gray mold (*Botrytis cinerea*), and sclerotinia rot (*Sclerotinia sclerotiorum*);

Diseases of Japanese radish: alternaria leaf spot (*Alternaria brassicicola*);

Turfgrass diseases: dollar spot (*Sclerotinia homeocarpa*), brown patch and large patch (*Rhizoctonia solani*);

Banana diseases: Sigatoka disease (*Mycosphaerella fijiensis, Mycosphaerella musicola*);

seed diseases or diseases in the early stages of the growth of various plants caused by caused by *Aspergillus* spp., *Penicillium* spp., *Fusarium* spp., *Gibberella* spp ., *Tricoderma* spp., *Thielaviopsis* spp., *Rhizopus* spp., *Mucor* spp., *Corticium* spp., *Phoma* spp., *Rhizoctonia* spp. or *Diplodia* spp.; and viral diseases of various plants mediated by *Polymixa* spp. or *Olpidium* spp.; and so on.

EXAMPLES

Next, the following Process for the present tetrazolinone compound, and the Examples including Formulation examples and Test examples, serve to illustrate the present invention in more detail, which should not intend to limit the present invention.

First, Preparation Example for the present tetrazolinone compound is shown.

Preparation Example 1

A mixture of 1-(2-bromomethyl-3-chlorophenyl)-4-methyl-1,4-dihydrotetrazole-5-one (described in Reference Preparation example 3) 1.21 g, 1-(4-chlorophenyl)-1H-pyrazole-3-ol 0.78 g, potassium carbonate 0.66 g and acetonitrile 30 mL was stirred with heating under reflux for four hours. To the reaction mixture after standing to cool was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-chlorophenyl)-1H-pyrazol-3-yl]oxymethyl}-3-chlorophenyl)-4-methyl-1,4-dihydrotetrazole-5-one (hereinafter referred to as Present tetrazolinone compound 1) 0.61 g.

Present tetrazolinone Compound 1

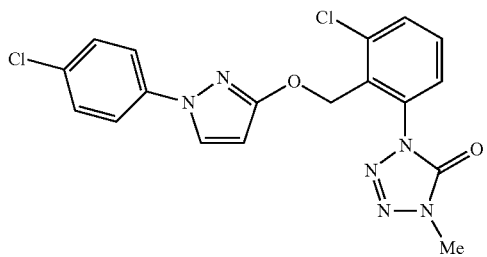

¹H-NMR (CDCl₃) δ(ppm): 7.64 (1H, d, J=2.7 Hz), 7.62-7.60 (1H, m), 7.53-7.49 (2H, m), 7.45 (1H, t, J=8.0 Hz), 7.39-7.35 (3H, m), 5.80 (1H, d, J=2.7 Hz), 5.54 (2H, s), 3.61 (3H, s).

Preparation Example 2

A mixture of 1-(2-bromomethyl-3-bromophenyl)-4-methyl-1,4-dihydrotetrazole-5-one (described in Reference Preparation Example 6) 18.5 g, 1-(4-chlorophenyl)-1H-pyrazole-3-ol 10.4 g, potassium carbonate 8.8 g and acetonitrile 400 mL was stirred with heating under reflux for four hours. To the reaction mixtures after standing to cool was added water and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-chlorophenyl)-1H-pyrazol-3-yl]oxymethyl}-3-bromophenyl)-4-methyl-1,4-dihydrotetrazole-5-one (hereinafter referred to as Present tetrazolinone compound 2) 24.6 g.

Present Tetrazolinone Compound 2

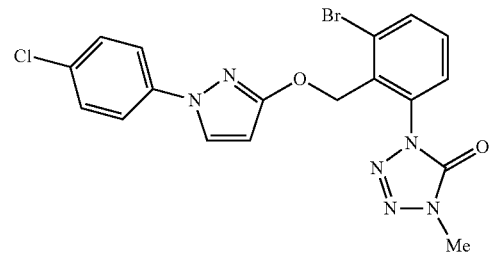 [SMILES: Cn1nnn(-c2cccc(Br)c2COc2ccn(-c3ccc(Cl)cc3)n2)c1=O]

¹H-NMR (CDCl₃) δ(ppm): 7.81-7.79 (1H, m), 7.65 (1H, d, J=2.4 Hz), 7.54-7.50 (2H, m), 7.42-7.35 (4H, m), 5.81 (1H, d, J=2.4 Hz), 5.53 (2H, s), 3.60 (3H, s)

Preparation Example 3

A mixture of the present tetrazolinone compound 2 (described in Preparation Example 2) 0.92 g, methyl boronic acid 0.18 g, tripotassium phosphate 1.27 g, water 0.11 mL, [1,1'-bis(diphenylphosphino)ferrocene]-palladium(II) dichloride dichloromethane complex 0.16 g, and dioxane 7 mL was stirred with heating under reflux for one and a half hours. To the reaction solution after cooling was added water, and the mixtures were extracted with ethyl acetate. The organic layer was washed with water and saturated saline, dried over anhydrous magnesium sulfate, and then concentrated under reduced pressure. The resulting residue was subjected to a silica gel column chromatography to give 1-(2-1[1-(4-chlorophenyl)-1H-pyrazol-3-yl]oxymethyl}-3 -methylphenyl)-4-methyl-1,4-dihydrotetrazole-5 -one (hereinafter referred to as Present tetrazolinone compound 3) 0.27 g.

Present Tetrazolinone Compound 3

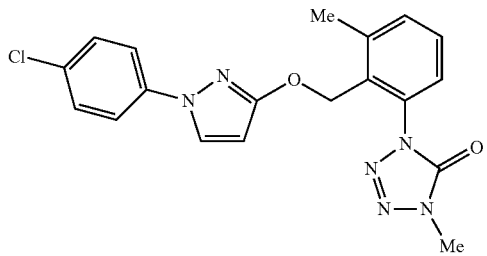 [SMILES: Cc1cccc(-n2nnn(C)c2=O)c1COc1ccn(-c2ccc(Cl)cc2)n1]

$^1$H-NMR (CDCl$_3$) δ(ppm): 7.64 (1H, d, J=2.7 Hz), 7.52-7.49 (2H, m), 7.42-7.35 (4H, m), 7.27-7.24 (1H, m), 5.82 (1H, d, J=2.7 Hz), 5.33 (2H, s), 3.63 (3H, s), 2.56 (3H, s)

Preparation Example 4

A mixture of 1-(2-bromomethyl-3-methylphenyl)-4-methyl-1,4-dihydrotetrazole-5-one (described in Reference Preparation Example 12) 0.30 g, 1-(4-methoxyphenyl)-1H-pyrazole-3-ol 0.21 g, potassium carbonate 0.19 g and acetonitrile 10 ml was stirred with heating under reflux for two hours. To the reaction mixtures after standing to cool was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-methoxyphenyl)-1H-pyrazol-3-yl]oxymethyl}-3-methylphenyl)-4-methyl-1,4-dihydrotetrazole-5-one (hereinafter referred to as Present tetrazolinone compound 4) 0.28 g.

Present Tetrazolinone Compound 4

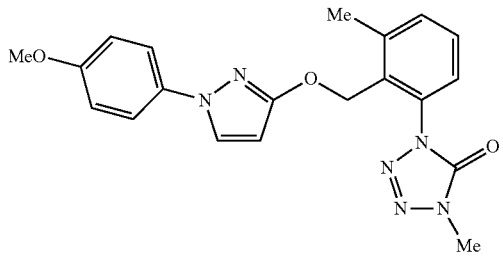 [SMILES: COc1ccc(-n2ccc(OCc3c(C)cccc3-n3nnn(C)c3=O)n2)cc1]

$^1$H-NMR (CDCl$_3$) δ(ppm): 7.57 (1H, d, J=2.7 Hz), 7.49-7.44 (2H, m), 7.39-7.36 (2H, m), 7.27-7.23 (1H, m), 6.96-6.91 (2H, m), 5.77 (1H, d, J=2.7 Hz), 5.32 (2H, s), 3.83 (3H, s), 3.61 (3H, s), 2.56 (3H, s).

Preparation Example 5

A mixture of 1-(2-bromomethyl-3-methoxyphenyl)-4-methyl-1,4-dihydrotetrazole-5-one (described in Reference Preparation Exmaple 9) 1.20 g, 1-(4-chlorophenyl)-1H-pyrazole-3-ol 0.78 g, potassium carbonate 0.66 g, and acetonitrile 30 mL was stirred with heating under reflux for four hours. To the reaction mixtures after standing to cool was added water and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-chlorophenyl)-1H-pyrazol-3-yl]oxymethyl}-3-methoxyphenyl)-4-methyl-1,4-dihydrotetrazole-5-one (hereinafter referred to as Present tetrazolinone compound 5) 0.97 g.

Present Tetrazolinone Compound 5

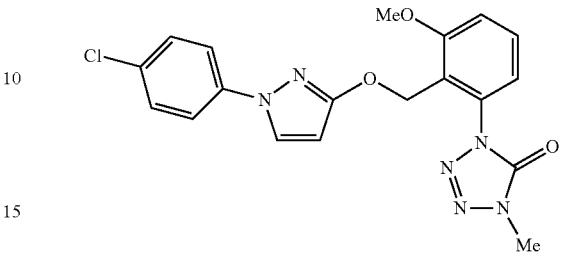

$^1$H-NMR (CDCl$_3$) δ(ppm): 7.63 (1H, d, J=2.7 Hz), 7.53-7.49 (2H, m), 7.46 (1H, dd, J=8.5, 8.0 Hz), 7.38-7.34 (2H, m), 7.08 (1H, d, J=8.5 Hz), 7.04 (1H, d, J=8.0 Hz), 5.80 (1H, d, J=2.7 Hz), 5.43 (2H, s), 3.92 (3H, s), 3.57 (3H, s).

Preparation Example 6

A mixture of present tetrazolinone compound 2 (described in Preparation Example 2) 0.92 g, ethyl boronic acid 0.22 g, tripotassium phosphate 1.27 g, water 0.11 mL, [1,1'-bis(diphenylphosphino)ferrocene]-palladium(II) dichloride dichloromethane complex 0.16 g and dioxane 15 mL was stirred with heating under reflux for two hours. To the reaction solution after cooling was added water, and the mixtures were extracted with ethyl acetate. The organic layers were washed with water and saturated saline, dried over anhydrous magnesium sulfate, and then concentrated under reduced pressure. The resulting residue was subjected to ,a silica gel column chromatography to give 1-(2-{[1-(4-chlorophenyl)-1H-pyrazol-3-yl]oxymethyl}3-ethylpenyl)-4-methyl-1,4-dihydroteterazole-5-one (hereinafter referred to as Present tetrazolinone compound 6) 0.24 g.

Present Tetrazolinone Compound 6

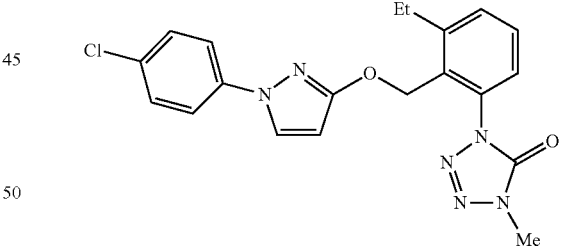

$^1$H-NMR (CDCl$_3$) δ(ppm): 7.65 (1H, d, J=2.7 Hz), 7.53-7.49 (2H, m), 7.47-7.42 (2H, m), 7.39-7.35 (2H, m), 7.27-7.24 (1H, m), 5.81 (1H, d, J=2.7 Hz), 5.34 (2H, s), 3.61 (3H, s), 2.90 (2H, q, J=7.6 Hz), 1.30 (3H, t, J=7.6 Hz).

Preparation Example 7

A mixture of present tetrazolinone compound 2 (described in Preparation Example 2) 0.92 g, cyclopropyl boronic acid 0.26 g, tripotassium phosphate 1.27 g, water 0.11 mL, [1,1'-bis(diphenylphosphino)]ferrocene]-palladium(II) dichloride dichloromethane complex 0.16 g, and dioxane 7 mL was stirred with heating under reflux for one and a half hours. To the reaction solution after cooling was added water, and the mixtures were extracted with ethyl acetate. The organic layers were washed with water and saturated saline, dried over anhydrous magnesium sulfate, and then concentrated under reduced pressure. The resulting residue was subjected to to a silica gel column chromatography to give 1-(2-{[1-(4-chlorophenyl)-1H-pyrazol-3-yl]oxymethyl}-3-cyclopropylphenyl)-4-methyl-1,4-dihydrotetrazole-5-one (hereinafter referred to as Present tetrazolinone compound 7) 0.35 g.

Present Tetrazolinone Compound 7

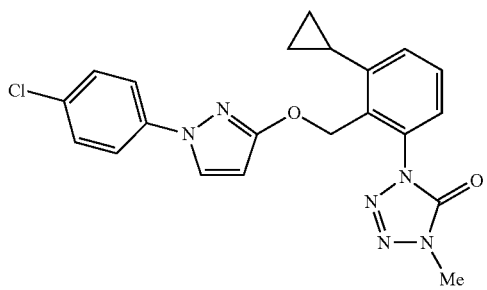 [SMILES: Cn1nnn(-c2cccc(C3CC3)c2COc2ccn(-c3ccc(Cl)cc3)n2)c1=O]

$^1$H-NMR (CDCl$_3$) δ(ppm): 7.63 (1H, d, J=2.7 Hz), 7.51-7.46 (2H, m), 7.41-7.37 (1H, m), 7.36-7.32 (2H, m), 7.24-7.21 (2H, m), 5.80 (1H, d, J=2.7 Hz), 5.53 (2H, s), 3.58 (3H, s), 2.26-2.19 (1H, m), 1.03-0.99 (2H, m), 0.78-0.74 (2H, m).

Preparation Example 8

A mixture of 1-(2-bromomethyl-3-methylphenyl)-4-methyl-1,4-dihydrotetrazole-5-one (described in Reference Preparation Example 12) 0.30 g, 1-(4-bromophenyl)-1H-pyrazole-3-ol 0.27 g, potassium carbonate 0.19 g, and acetonitrile 10 mL was stirred with heating under reflux for four hours. To the reaction mixtures after standing to cool was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-bromophenyl)-1H-pyrazol-3-yl]oxymethyl}-3-methylpheny)-4-methyl-1,4-dihydrotetrazole-5-one (hereinafter referred to as Present tetrazolinone compound 8) 0.37 g.

Present Tetrazolinone Compound 8

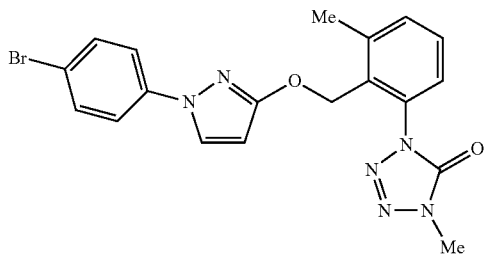

$^1$H-NMR (CDCl$_3$) δ(ppm): 7.64 (1H, d, J=2.4 Hz), 7.53-7.49 (2H, m), 7.45-7.37 (4H, m), 7.27-7.24 (1H, m), 5.82 (1H, d, J=2.4 Hz), 5.33 (2H, s), 3.62 (3H, s), 2.55 (3H, s).

Preparation Example 9

A mixture of 1-(2-{[1H-pyrazol-3-yl]oxymethyl}-3-methylphenyl)-4-methyl-1,4-dihydrotetrazole-5-one (described in Reference Preparation Example 14) 0.49 g, 4-chloro-3-flurophenylboronic acid 0.33 g, copper(II) acetate 0.51 g, pyridine 0.28 g, molecular sieve 4A 1.00 g, and acetonitrile 10 mL was stirred with heating under reflux for forty eight hours. To the reaction mixtures after standing to cool was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-chloro-3-fluorophenyl)-1H-pyrazol-3yl]oxymethyl}-3-methylphenyl)-4-methyl-1,4-dihydrotetrazole-5-one (hereinafter referred to as Present tetrazolinone compound 9) 0.12 g.

Present Tetrazolinone Compound 9

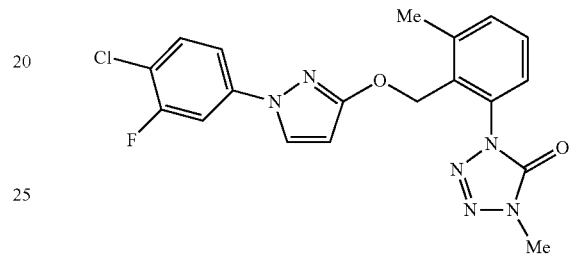

$^1$H-NMR (CDCl$_3$) δ(ppm): 7.64 (1H, d, J=2.7 Hz), 7.44-7.38 (4H, m), 7.28-7.23 (2H, m), 5.84 (1H, d, J=2.7 Hz), 5.33 (2H, s), 3.65 (3H, s), 2.56 (3H, s).

Preparation Example 10

A mixture of 1-(2-bromomethyl-3-methylpenyl)-4-methyl-1,4-dihydrotetrazole-5-one (described in Reference Preparation Example 12) 0.30 g, 1-(2-methoxyphenyl)-1H-pyrazole-3-ol 0.20 g, potassium carbonate 0.19 g and acetonitrile 10 mL was stirred with heating under reflux for four hours. To the reaction mixtures after standing to cool was added water, and the mixtures were extracted with ethyl acetate. The organic layers were washed with water and saturated saline, dried over anhydrous magnesium sulfate, and then concentrated under reduced pressure. The resulting residue was subjected to silica gel column chromatography to give 1-(2-{[1-(2-methoxyphenyl)-1H-pyrazol-3-yl]oxymethyl}-3-methylphenyl)-4-methyl-1,4-dihydrotetrazole-5-one (hereinafter referred to as Present tetrazolinone compound 10) 0.23 g.

Present Tetrazolinone Compound 10

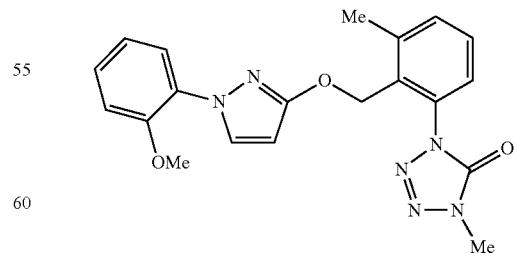

$^1$H-NMR (CDCl$_3$) δ(ppm): 7.89 (1H, d, J=2.5 Hz), 7.70 (1H, dd, J=8.0, 1.6 Hz), 7.41-7.37 (2H, m), 7.26-7.18 (2H, m), 7.06-6.99 (2H, m), 5.76 (1H, d, J=2.5 Hz), 5.32 (2H, s), 3.88 (3H, s), 3.61 (3H, s), 2.55 (3H, s).

Preparation Example 11

A mixture of 1-(2-{[1H-pyrazol-3-yl]oxymethyl}-3-methylphenyl)-4-methyl-1,4-dihydroteterazole-5-one (described in Reference Preparation Example 14) 1.00 g, 4-chloro-2-methoxyphenyl boronic acid 0.78 g, copper(II) acetate 0.98 g, pyridine 0.59 mL, molecular sieve 4A 1.50 g, and acetonitrile 15 mL was stirred with heating under reflux for fifteen hours. To the reaction mixtures after standing to cool was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-(4-chloro-2-methoxyphenyl)-1H-pyrazol-3-yl]oxymethyl}-3-methylphenyl)-4-methyl-1,4-dihydroteterazole-5-one (hereinafter referred to as Present tetrazolinone compound 11) 0.15 g.

Present Tetrazolinone Compound 11

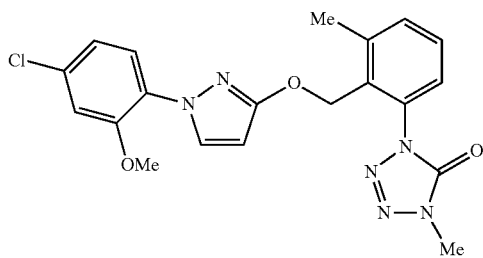 [SMILES: COc1cc(Cl)ccc1-n1ccc(OCc2c(C)cccc2-n2nnn(C)c2=O)n1]

$^1$H-NMR (CDCl$_3$) δ: 7.87 (1H, d, J 32 2.5 Hz), 7.65 (1H, d, J=8.5 Hz), 7.42-7.37 (2H, m), 7.26-7.24 (1H, m), 7.03 (1H, dd, J 32 8.5, 2.3 Hz), 6.99 (1H, d, J=2.3 Hz), 5.77 (1H, d, J=2.5 Hz), 5.30 (2H, s), 3.89 (3H, s), 3.63 (3H, s), 2.55 (3H, s).

Next, processes for preparing intermediates of the above-mentioned Present tetrazolinone compound are shown below as Reference Preparation Examples.

Reference Preparation Example 1

Anhydrous aluminium chloride 21.9 g was added to N,N-dimethylformamide 250 mL under ice-cooling, and the mixtures were stirred for fifteen minutes. Thereto was added sodium azide 10.7 g and the mixtures were stirred for fifteen minutes. Thereto was then added 1-chloro-3-isocyanato-2-methylbenzene 25.0 g, and the resulting mixtures were heated at 80° C. for five hours. The reaction solutions after cooling were added to a mixture of sodium nitrite 35 g, water 2 L and ice 500 g with stirring. The mixtures were acidified with 10% hydrochloric acid and were extracted with ethyl acetate. The organic layers were washed with water and saturated saline, dried over anhydrous magnesium sulfate, and then concentrated under reduced pressure to give 1-(2-methyl-3-chlorophenyl)-1,4-dihydrotetrazole-5-one 17.0 g.

1-(2-methyl-3-chlorophenyl)-1,4-dihydrotetrazole-5-one

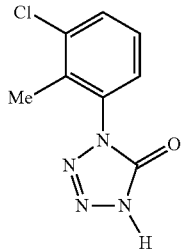 [SMILES: Cc1c(Cl)cccc1-n1nn[nH]c1=O]

$^1$H-NMR (CDCl$_3$) δ(ppm): 2.32 (3H, s), 7.28-7.36 (2H, m), 7.57 (1H, dd, J=6.8, 2.2 Hz), 13.08 (1H, s).

Reference Preparation Example 2

To a mixture of 1-(2-methyl-3-chlorophenyl)-1,4-dihydrotetrazole-5-one (described in Reference Preparation Example 1) 10.00 g and N,N-dimethylformamide 100 mL was added 60% sodium hydride 2.30 g under ice-cooling. The mixtures were raised to room temperature and were stirred for one hour. To the reaction mixtures was added methyl iodide 3.2 mL under ice cooling. The mixtures were raised to room temperature and stirred for fourteen hours. To the reaction mixtures was added water, and the mixtures were extracted with ethyl acetate. The organic layers were washed with 10% hydrochloric acid, water and saturated saline, and was dried over anhydrous magnesium sulfate, and then concentrated under reduced pressure. The resulting residue was subjected to a silica gel column chromatography to give 1-(2-methyl-3-chlorophenyl)-4-methyl-1,4-dihydrotetrazole-5-one 1.56 g.

1-(2-methyl-3-chlorophenyl)-4-methyl-1,4-dihydrotetrazole-5-one

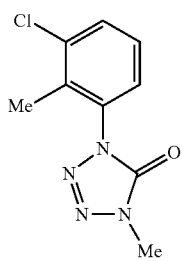 [SMILES: Cc1c(Cl)cccc1-n1nnn(C)c1=O]

$^1$H-NMR (CDCl$_3$) δ(ppm): 2.30 (3H, s), 3.73 (3H, s), 7.27 (1H, d, J=2.7 Hz), 7.28 (1H, d, J=7.1 Hz), 7.52 (1H, dd, J=2.7, 6.8 Hz).

Reference Preparation Example 3

A mixture of 1-(2-methyl-3-chlorophenyl)-4-methyl-1,4-dihydrotetrazole-5-one (described in Reference Example 2) 1.56 g, 1,1'-azobis(cyclohexane-1-carbonitrile) 0.34 g, N-bromosuccinimide 1.42 g and chlorobenzene 30 mL was stirred with heating under reflux for five hours. To the reaction solutions after cooling was added water, and the mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-bromomethyl-3-chlorophenyl)-4-methyl-1,4-dihydrotetrazole-5-one 1.94 g.

1-(2-bromomethyl-3-chlorophenyl)-4-methyl-1,4-dihydrotetrazole-5-one

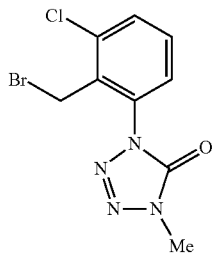 [SMILES: Cn1nnn(-c2cccc(Cl)c2CBr)c1=O]

$^1$H-NMR (CDCl$_3$) δ(ppm): 3.76 (3H, s), 4.69 (2H, s), 7.35 (1H, dd, J=1.2, 8.1 Hz), 7.43 (1H, t, J=8.1 Hz), 7.58 (1H, dd, J=1.2, 8.1 Hz).

Reference Preparation Examples 4

Anhydrous aluminium chloride 19.7 g was added to N,N-dimethylformamide 220 mL under ice-cooling, and the mixture was stirred for fifteen minutes. Thereto was added sodium azide 9.6 g and the mixtures were stirred for fifteen minutes. Thereto was then added 1-bromo-3-isocyanato-2-methylbenzene 30.3 g and the resulting mixtures were heated at 80° C. for five hours. The reaction solutions after cooling were added to a mixture of sodium nitrite 33 g, water 2 L and ice 500 g with stirring. The mixtures were acidified with 10% hydrochloric acid, and were extracted with ethyl acetate. The organic layers were washed with water and saturated saline and then were dried over anhydrous magnesium sulfate and were then concentrated under reduced pressure to give 1-(2-methyl-3-bromophenyl)-1,4-dihydrotetrazole-5-one 31.4 g.

1-(2-methyl-3-bromophenyl)-1,4-dihydrotetrazole-5-one

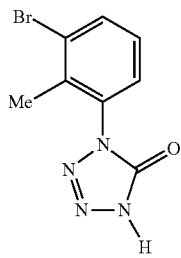

$^1$H-NMR (DMSO-d$_6$) δ(ppm): 2.22 (3H, s), 7.34 (1H, t, J=7.2 Hz), 7.49 (1H, dd, J=8.2, 1.1 Hz), 7.82 (1H, dd, J=8.0, 1.0 Hz), 14.72 (1H, s).

Reference Preparation Example 5

To a mixture of 1-(2-methyl-3-bromophenyl)-1,4-dihydrotetrazole-5-one (described in Reference Preparation Example 4) 31.40 g and N,N-dimethylformamide 250 mL was added 60% sodium hydride 5.90 g under ice-cooling. The reaction mixtures were raised to room temperature, and were stirred for one hour. To the reaction mixtures was added methyl iodide 8.4 mL under ice-cooling. The mixtures were raised to room temperature, and were stirred for fourteen hours. To the reaction mixtures was added water and the mixtures were extracted with ethyl acetate. The organic layers were washed with 10% hydrochloric acid, water and saturated saline, and dried over anhydrous magnesium sulfate and then concentrated under reduced pressure. The resulting residues were subjected to a silica gel column chromatography to give 1-(2-methyl-3-bromophenyl)-4-methyl-1,4-dihydrotetrazole-5-one 8.47 g.

1-(2-methyl-3-bromophenyl)-4-methyl-1,4-dihydrotetrazole-5-one

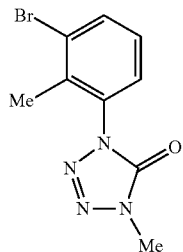 [SMILES: Cc1c(Br)cccc1-n1nn[nH]c1=O]

$^1$H-NMR (CDCl$_3$) δ(ppm): 2.33 (3H, s), 3.73 (3H, s), 7.21 (1H, dt, J=0.5, 7.8 Hz), 7.30 (1H, dd, J=1.0, 8.0 Hz), 7.71 (1H, dd, J=1.2, 8.3 Hz).

Reference Preparation Example 6

To a mixture of 1-(2-methyl-3-bromophenyl)-4-methyl-1,4-dihydrotetrazole-5-one (described in Reference Preparation Example 5) 8.47 g, 1,1'-azobis(cyclohexane-1-carbonitrile) 1.54 g, N-bromosuccinimide 6.44 g and chlorobenzene 125 mL was stirred with heating under reflux for five hours. To the reaction solutions after cooling was added water and the resulting mixtures were extracted with ethyl acetate. The organic layers were washed with water and saturated saline, and dried over anhydrous magnesium sulfate and then concentrated under reduced pressure. The resulting residues were subjected to a silica gel column chromatography to give 1-(2-bromomethyl-3-bromophenyl)-4-methyl-1,4-dihydrotetrazole-5-one 7.52 g.

1-(2-bromomethyl-3-bromophenyl)-4-methyl-1,4-dihydrotetrazole-5-one

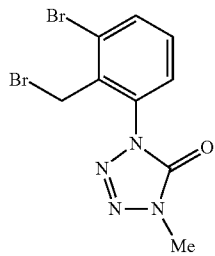 [SMILES: Cn1nnn(-c2cccc(Br)c2CBr)c1=O]

$^1$H-NMR (CDCl$_3$) δ(ppm): 3.76 (3H, s), 4.71 (2H, s), 7.34 (1H, t, J=7.8 Hz), 7.38 (1H, dd, J=8.0, 1.7 Hz), 7.77 (1H, dd, J=7.8, 1.7 Hz).

Reference Preparation Example 7

Anhydrous aluminium chloride 16.0 g was added to N,N-dimethylformamide 180 mL under ice-cooling, and the mixtures were stirred for fifteen minutes. Thereto was added sodium azide 7.8 g and the mixtures were stirred for fifteen minutes. Thereto was then added 1-methoxy-3-isocyanato-2-methylbenzene 17.0 g, and the resulting mixtures were heated at 80° C. for four and a half hours. The reaction solutions after cooling were added to a mixture of sodium nitrite 25 g, water 2 L and ice 500 g with stirring. The mixtures were acidified with 10% hydrochloric acid and were extracted with ethyl acetate. The organic layers were washed with water and saturated saline, dried over anhydrous magnesium sulfate, and then concentrated under reduced pressure to give 1-(2-methyl-3-methoxyphenyl)-1, 4-dihydrotetrazole-5-one 16.2 g.

1-(2-methyl-3-methoxyphenyl)-1,4-dihydrotetrazole-5-one

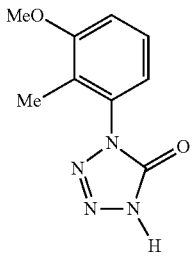 [SMILES: COc1cccc(-n2nn[nH]c2=O)c1C]

$^1$H-NMR (DMSO-d$_6$) δ(ppm): 1.99 (3H, s), 3.87 (3H, s), 7.01 (1H, d, J=8.1 Hz), 7.17 (1H, d, J=8.1 Hz). 7.36 (1H, t, J=8.3 Hz), 14.63 (1H, s).

Reference Preparation Example 8

To a mixture of 1-(2-methyl-3-methoxyphenyl)-1,4-dihydrotetrazole-5-one (described in Reference Preparation Example 7) 10.00 g and N,N-dimethylformamide 100 mL was added 60% sodium hydride 2.47 g under ice-cooling. The reaction mixtures were raised to room temperature and were stirred for fourteen hours. To the reaction mixtures was added methyl iodide 3.5 mL under ice-cooling. The mixtures were raised to room temperature and were stirred for one hour. To the reaction mixtures was added methyl iodide 3.5 mL under ice-cooling. The mixtures were raised to room temperature and stirred for fourteen hours. To the reaction mixtures was added water and the mixtures were extracted with ethyl acetate. The organic layers were washed with 10% hydrochloric acid, water and saturated saline, dried over anhydrous magnesium sulfate, and then concentrated under reduced pressure. The resulting residues were subjected to a silica gel column chromatography to give 1-(2-methyl-3-methoxyphenyl)-4-methyl-1,4-dihydrotetrazole-5-one 2.19 g.

1-(2-methyl-3-methoxyphenyl)-4-methyl-1,4-dihydrotetrazole-5-one

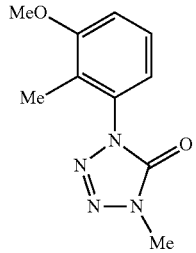 [SMILES: COc1cccc(-n2nnn(C)c2=O)c1C]

$^1$-NMR (CDCl$_3$) δ(ppm): 2.11 (3H, s), 3,72 (3H, s) , 3.88 (3H, s), 6.95 (1H, d, J=8.2 Hz), 6.98 (1H, d, J=8.5 Hz), 7.29 (1H, t, J=8.2 Hz)

Reference Preparation Example 9

To a mixture of 1-(2-methyl-3-methoxyphenyl)-4-methyl-1,4-dihydrotetrazole-5-one (described in Reference Preparation Example 8) 2.19 g, 1,1'-azobis(cyclohexane-1-carbonitrile) 0.52 g, N-bromosuccinimide 2.16 g and chlorobenzene 40 mL was stirred with heating under reflux for five hours. To the reaction solutions after cooling was added water, and the resulting mixtures were extracted with ethyl acetate. The organic layers were washed with water and saturated saline, dried over anhydrous magnesium sulfate, and then concentrated under reduced pressure. The resulting residues were subjected to a silica gel column chromatography to give 1-(2-bromomethyl-3-methoxyphenyl)-4-methyl-1,4-dihydrotetrazole-5-one 2.36 g.

1-(2-bromomethyl-3-methoxyphenyl)-4-methyl-1,4-dihydrotetrazole-5-one

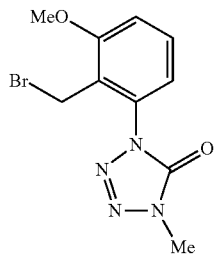 [SMILES: COc1cccc(-n2nnn(C)c2=O)c1CBr]

$^1$H-NMR (CDCl$_3$) δ(ppm): 3.74 (3H, s), 3.96 (3H, s) , 4.93 (2H, s), 7.02 (1H, dd, J=1.0, 8.5 Hz), 7.04 (1H, d, J=9.0 Hz), 7.43 (1H, t, J=8.1 Hz).

Reference Preparation Example 10

A mixture of 1-(2-bromomethyl-3-bromophenyl)-4-methyl-1,4-dihydrotetrazole-5-one (described in Reference Preparation Example 6) 45.0 g, sodium methoxide 37.4 g and tetrahydrofuran 600 mL was stirred at room temperature for three hours. To the reaction mixtures was added aqueous saturated sodium bicarbonate solution, and the resulting mixtures were extracted with ethyl acetate. The organic layers were washed with aqueous saturated sodium bicarbonate solution, and then dried over anhydrous sodium sulfate. The mixtures were concentrated under reduced pressure to give 1-(2-methoxymethyl-3-bromophenyl)-4-methyl-1,4-dihydrotetrazole-5-one 36.2 g.

1-(2-methoxymethyl-3-bromophenyl)-4-methyl-1,4-dihydrotetrazole-5-one

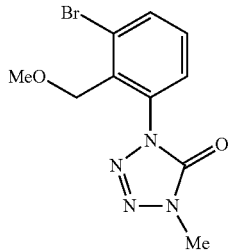 [SMILES: COCc1c(Br)cccc1-n1nnn(C)c1=O]

¹H-NMR (CDCl₃) δ(ppm): 3.23 (3H, s), 3.72 (3H, s), 4.67 (2H, s), 7.33 (1H, t, J=7.8 Hz), 7.38 (1H, dd, J=1.2, 8.1 Hz), 7.76 (1H, dd, J=1.5, 7.8 Hz).

Reference Preparation Example 11

A mixture of 1-(2-methoxymethyl-3-bromophenyl)-4-methyl-1,4-dihydrotetrazole-5-one (described in Reference Preparation Example 10) 36.2 g, methylboronic acid 23.2 g, cesium fluoride 66.7 g, [1,1'-bis(diphenylphosphino)ferrocene]palladium(II) dichloride dichloromethane adduct 10.6 g and dioxane 500 mL was stirred at 90° C. for five and a half hours. The reaction mixtures after cooling were filtered, and the filtrates were concentrated under reduced pressure. The resulting residues were subjected to a silica gel column chromatography to give 1-(2-methoxymethyl-3-methylphenyl)-4-methyl-1,4-dihydrotetrazole-5-one 25.6 g.

1-(2-methoxymethyl-3-methylphenyl)-4-methyl-1,4-dihydrotetrazole-5-one

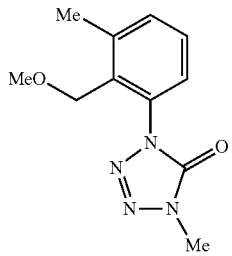 [SMILES: COCc1c(C)cccc1-n1nnn(C)c1=O]

¹H-NMR (CDCl₃) δ(ppm): 2.48 (3H, s), 3.23 (3H, s), 3.72 (3H, s), 4.42 (2H, s), 7.21 (1H, t, J=5.1 Hz), 7.35 (2H, d, J=4.8 Hz).

Reference Preparation Example 12

A mixture of 1-(2-methoxymethyl-3-methylphenyl)-4-methyl-1,4-dihydrotetrazole-5-one (described in Reference Preparation Example 11) 25.6 g, acetic acid 50 mL and 25% hydrogen bromide-acetic acid solution 50 mL was stirred at 65° C. for one hour. To the reaction mixtures was added saturated saline, and the mixtures were extracted with ethyl acetate. The organic layers were washed with aqueous saturated sodium bicarbonate solution and were then dried over anhydrous sodium sulfate. The mixtures were concentrated under reduced pressure to give 1-(2-bromomethyl-3-methylphenyl)-4-methyl-1,4-dihydrotetrazole-5-one 27.9 g.

1-(2-bromomethyl-3-methylphenyl)-4-methyl-1,4-dihydrotetrazole-5-one

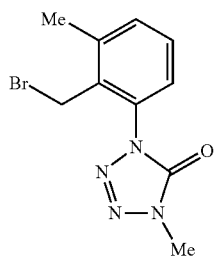 [SMILES: Cc1cccc(-n2nnn(C)c2=O)c1CBr]

¹H-NMR (CDCl₃) δ(ppm): 2.51 (3H, s), 3.75 (3H, s), 4.51 (2H, s), 7.22-7.24 (1H, m), 7.36-7.39 (2H, m).

Reference Preparation Example 13

A mixture of 1-(2-bromomethyl-3-methylphenyl)-4-methyl-1,4-dihydrotetrazole-5-one (described in Reference Preparation Example 12) 1.0 g, 1-acetyl-1H-pyrazole-3-ol 0.47 g, potassium carbonate 0.63 g and acetonitrile 20 mL was stirred with heating under reflux for two hours. To the reaction mixtures after standing to cool was added water, and the resulting mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1-acetyl-1H-pyrazol-3-yl]oxymethyl}-3-methylphenyl)-4-methyl-1,4-dihydrotetrazole-5-one 0.58 g.

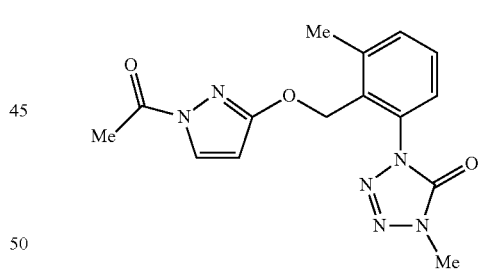

¹H-NMR (CDCl₃) δ(ppm): 8.01 (1H, d, J=2.9 Hz), 7.43-7.38 (2H, m), 7.26 (1H, dd, J=6.9, 2.1 Hz), 5.88 (1H, d, J=2.9 Hz), 5.31 (2H, s), 3.69 (3H, s), 2.55 (3H, s), 2.54 (3H, s).

Reference Preparation Example 14

A mixture of 1-(2-{[1-acetyl-1H-pyrazol-3-yl]oxymethyl}-3-methylphenyl)-4-methyl-1,4-dihydrotetrazole-5-one (described in Reference Preparation Example 13) 3.4 g, sodium methoxide 0.59 g and methanol 30 mL was stirred at room temperature for two hours. The reaction mixtures were added to aqueous saturated sodium bicarbonate solution, and the resulting mixtures were extracted with ethyl acetate. The organic layers were washed with water and saturated saline, dried over anhydrous magnesium sulfate, and then concentrated under reduced pressure. The resulting residue was subjected to a silica gel column chromatography to give 1-(2-{[1H-pyrazol-3-yl]oxymethyl}-3-methylphenyl)-4-methyl-1,4-dihydrotetrazole-5-one 2.5 g.

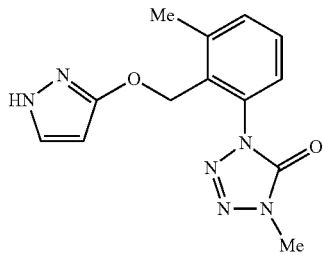 [SMILES: Cc1cccc(-n2nnn(C)c2=O)c1COc1cc[nH]n1]

$^1$H-NMR (CDCl$_3$) δ(ppm): 9.61 (1H, s), 7.40-7.35 (2H, m), 7.27 (1H, d, J=2.4 Hz), 7.24 (1H, dd, J=6.5, 2.8 Hz), 5.63 (1H, d, J=2.4 Hz), 5.23 (2H, d, J=11.2 Hz), 3.66 (3H, s), 2.52 (3H, s).

The compounds selected from the present tetrazolinone compound 12 to the present tetrazolinone compound 81, which can be prepared according to the above-mentioned Process A to Process C, are shown below.

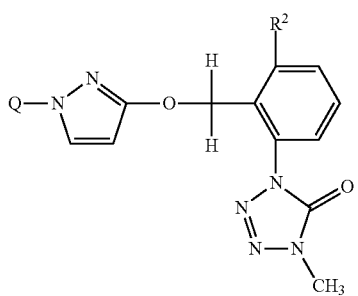

(1)

TABLE 2

| Present tetrazolinone compound | Q | R² |
|---|---|---|
| 12 | 4-chlorophenyl | fluoro |
| 13 | 4-fluorophenyl | chloro |
| 14 | 4-methylphenyl | chloro |
| 15 | 4-methoxyphenyl | chloro |
| 16 | 4-fluorophenyl | bromo |
| 17 | 4-methoxyphenyl | bromo |
| 18 | 4-chlorophenyl | iodo |
| 19 | phenyl | methyl |
| 20 | 4-fluorophenyl | methyl |
| 21 | 4-methylphenyl | methyl |
| 22 | 4-cyanophenyl | methyl |
| 23 | 4-methylthiophenyl | methyl |
| 24 | 3-fluoro-4-methoxyphenyl | methyl |
| 25 | 4-ethoxyphenyl | methyl |
| 26 | 3-fluoro-4-methylphenyl | methyl |
| 27 | 2-fluoro-4-methylphenyl | methyl |
| 28 | 4-fluorophenyl | methoxy |
| 29 | 4-methylphenyl | methoxy |
| 30 | 4-methoxyphenyl | methoxy |
| 31 | 4-chlorophenyl | difluoromethyl |
| 32 | 4-chlorophenyl | trifluoromethyl |

TABLE 2-continued

| Present tetrazolinone compound | Q | R² |
|---|---|---|
| 33 | 4-chlorophenyl | 1-propenyl |
| 34 | 4-chlorophenyl | propyl |
| 35 | 4-chlorophenyl | isopropyl |

TABLE 3

| Present tetrazolinone compound | Q | R² |
|---|---|---|
| 36 | 4-chlorophenyl | ethenyl |
| 37 | 4-chlorophenyl | 2-propenyl |
| 38 | 4-chlorophenyl | 1-methylethenyl |
| 39 | 4-chlorophenyl | ethynyl |
| 40 | 4-bromophenyl | chloro |
| 41 | 4-bromophenyl | bromo |
| 42 | 4-bromophenyl | methoxy |
| 43 | 4-trifluoromethoxyphenyl | methyl |
| 44 | 4-fluorophenyl | cyclopropyl |
| 45 | 4-fluorophenyl | ethyl |
| 46 | 4-bromophenyl | ethyl |
| 47 | 4-bromophenyl | cyclopropyl |
| 48 | 3-methylthiophenyl | methyl |
| 49 | 4-methoxyphenyl | ethyl |
| 50 | 4-methoxyphenyl | cyclopropyl |
| 51 | 4-methylphenyl | cyclopropyl |
| 52 | 4-methylphenyl | ethyl |
| 53 | 4-methylphenyl | bromo |
| 54 | 2-methylthiophenyl | methyl |
| 55 | 2,3,4,5,6-pentafluorophenyl | methyl |
| 56 | 2-chlorophenyl | methyl |
| 57 | 4-chlorophenyl | ethoxy |
| 58 | 4-fluorophenyl | ethoxy |
| 59 | 4-methoxyphenyl | ethoxy |

TABLE 4

| Present tetrazolinone compound | Q | R² |
|---|---|---|
| 60 | 4-bromophenyl | ethoxy |
| 61 | phenyl | ethoxy |
| 62 | 4-chlorophenyl | methylthio |
| 63 | 3-chlorophenyl | methyl |
| 64 | 4-nitrophenyl | methyl |
| 65 | 2-fluorophenyl | methyl |
| 66 | 2-methylphenyl | methyl |
| 67 | 2-bromophenyl | methyl |
| 68 | 3-fluorophenyl | methyl |
| 69 | 3-methylphenyl | methyl |
| 70 | 3-bromophenyl | methyl |
| 71 | 3-methoxyphenyl | methyl |
| 72 | 2-methoxyphenyl | chloro |
| 73 | 2-methoxyphenyl | methoxy |
| 74 | 2-methoxyphenyl | ethyl |
| 75 | 2-methoxyphenyl | cyclopropyl |
| 76 | 4-ethylphenyl | methyl |
| 77 | 4-trifluoromethylphenyl | methyl |
| 78 | 5-chloro-2-methoxyphenyl | methyl |
| 79 | 2-ethoxyphenyl | methyl |
| 80 | 2-isopropoxyphenyl | methyl |
| 81 | 3-chloro-2-methoxyphenyl | methyl |

Examples of an embodiment of the present tetrazolinone compound include the compounds represented by the formula (1) wherein the substituents represent the following ones.

a tetrazolinone compound represented by the formula (1) wherein n is an integer of any one of 0 to 2; R$^1$ represents a halogen atom, a C1-C6 alkyl group, a C1-C6 alkoxy group, a C1-C6 alkylthio group, a nitro group or a cyano group; and $R^2$ represents a methyl group, a cyclopropyl group, a chloro atom, a bromo atom, an ethyl group, or a methoxy group;

a tetrazolinone compound represented by the formula (1) wherein n is an integer of any one of 0 to 2; $R^1$ represents a halogen atom, a methyl group, an ethyl group, or a methoxy group; and $R^2$ represents a C1-C3 alkyl group, a C3-C4 cycloalkyl group, a halogen atom, a C2-C3 alkenyl group, a C1-C3 alkoxy group, a C1-C2 alkylthio group, or a C2-C3 alkynyl group;

a tetrazolinone compound represented by the formula (1) wherein n is an integer of any one of 0 to 2; $R^1$ represents a halogen atom, a methyl group, an ethyl group, or a methoxy group; and $R^2$ represents a methyl group, a cyclopropyl group, a chloro atom, a bromo atom, an ethyl group, or a methoxy group;

a tetrazolinone compound represented by the formula (1) wherein n is an integer of any one of 0 to 2; $R^1$ represents a halogen atom, a C1-C6 alkyl group, a C1-C6 alkoxy group, a C1-C6 alkylthio group, a nitro group, or a cyano group, a tetrazolinone compound represented by the formula (1) wherein n is an integer of any one of 0 to 2; and $R^1$ represents a halogen atom, a methyl group, an ethyl group, or a methoxy group;

a tetrazolinone compound represented by the formula (1) wherein $R^2$ represents a C1-C3 alkyl group, a C3-C4 cycloalkyl group, a halogen atom, a C2-C3 alkenyl group, a C1-C3 alkoxy group, a C1-C2 alkylthio group, or a C2-C3 alkynyl group;

a tetrazolinone compound represented by the formula (1) wherein $R^2$ represents a methyl group, a cyclopropyl group, a chloro atom, a bromo atom, an ethyl group, or a methoxy group;

a tetrazolinone compound represented by the formula (1) wherein $R^2$ represents a C1-C3 alkyl group;

a tetrazolinone compound represented by the formula (1) wherein $R^2$ represents a methyl group;

a tetrazolinone compound represented by the formula (1) wherein $R^2$ represents an ethyl group;

a tetrazolinone compound represented by the formula (1) wherein $R^2$ represents a C3-C4 cycloalkyl group;

a tetrazolinone compound represented by the formula (1) wherein $R^2$ represents a cyclopropyl group;

a tetrazolinone compound represented by the formula (1) wherein $R^2$ represents a halogen atom;

a tetrazolinone compound represented by the formula (1) wherein $R^2$ represents a chloro atom;

a tetrazolinone compound represented by the formula (1) wherein $R^2$ represents a bromo atom;

a tetrazolinone compound represented by the formula (1) wherein $R^2$ represents a C1-C3 alkoxy group; and a tetrazolinone compound represented by the formula (1) wherein $R^2$ represents a methoxy group.

Examples of an embodiment of the composition of the present invention include the following ones.

a composition for controlling plant diseases comprising a tetrazolinone compound represented by the formula (1) wherein n is an integer of 1 or 2, $R^1$ represents a halogen atom or a C1-C6 alkoxy group, $R^2$ represents a C1-C3 alkyl group, a C3-C4 cycloalkyl group, a halogen atom, or a C1-C3 alkoxy group, and any one of Compounds I to VI;

a composition for controlling plant diseases comprising a tetrazolinone compound represented by the formula (1) wherein n is an integer of 1 or 2, $R^1$ represents a halogen atom or a C1-C3 alkoxy group, $R^1$ represents a C1-C3 alkyl group, a C3-C4 cycloalkyl group, a halogen atom or a C1-C3 alkoxy group, and any one of Compounds I to VI;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound I;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound II;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound III;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound IV;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound V;

a composition for controlling plant diseases comprising a tetrazolinone compound represented by the formula (1) wherein n is an integer of 1 or 2, $R^1$ represents a halogen atom or a C1-C6 alkoxy group, and $R^2$ represents a C1-C3 alkyl group, a C3-C4 cycloalkyl group, a halogen atom or a C1-C3 alkoxy group, and Compound VI;

a composition for controlling plant diseases comprising any one of compounds selected from the present tetrazolinone compound 1 to the present tetrazolinone compound 81 and Compound I in the ratio of 0.1/1;

a composition for controlling plant diseases wherein comprising any one of compounds selected from the present tetrazolinone compound 1 to the present tetrazolinone compound 81 and Compound I in the ratio of 1/1;

a composition for controlling plant diseases comprising any one of compounds selected from the present tetrazolinone compound 1 to the present tetrazolinone compound 81 and Compound I in the ratio of 10/1;

a composition for controlling plant diseases comprising any one of compounds selected from the present tetrazolinone compound 1 to the present tetrazolinone compound 81 and Compound II in the ratio of 0.1/1;

a composition for controlling plant diseases comprising any one of compounds selected from the present tetrazolinone compound 1 to the present tetrazolinone compound 81 and Compound II in the ratio of 1/1;

a composition for controlling plant diseases comprising any one of compounds selected from the present tetrazolinone compound 1 to the present tetrazolinone compound 81 and Compound II in the ratio of 10/1;

a composition for controlling plant diseases comprising any one of compounds selected from the present tetrazolinone compound 1 to the present tetrazolinone compound 81 and Compound III in the ratio of 0.1/1;

a composition for controlling plant diseases comprising any one of compounds selected from the present tetrazolinone compound 1 to the present tetrazolinone compound 81 and Compound III in the ratio of 1/1;

a composition for controlling plant diseases comprising any one of compounds selected from the present tetrazolinone compound 1 to the present tetrazolinone compound 81 and Compound III in the ratio of 10/1;

a composition for controlling plant diseases comprising any one of compounds selected from the present tetrazolinone compound 1 to the present tetrazolinone compound 81 and Compound IV in the ratio of 0.1/1;

a composition for controlling plant diseases comprising any one of compounds selected from the present tetrazolinone compound 1 to the present tetrazolinone compound 81 and Compound IV in the ratio of 1/1;

a composition for controlling plant diseases comprising any one of compounds selected from the present tetrazolinone compound 1 to the present tetrazolinone compound 81 and Compound IV in the ratio of 10/1;

a composition for controlling plant diseases comprising any one of compounds selected from the present tetrazolinone compound 1 to the present tetrazolinone compound 81 and Compound V in the ratio of 0.1/1;

a composition for controlling plant diseases comprising any one of compounds selected from the present tetrazolinone compound 1 to the present tetrazolinone compound 81 and Compound V in the ratio of 1/1;

a composition for controlling plant diseases comprising any one of compounds selected from the present tetrazolinone compound 1 to the present tetrazolinone compound 81 and Compound V in the ratio of 10/1;

a composition for controlling plant diseases comprising any one of compounds selected from the present tetrazolinone compound 1 to the present tetrazolinone compound 81 and Compound VI in the ratio of 0.1/1;

a composition for controlling plant diseases comprising any one of compounds selected from the present tetrazolinone compound 1 to the present tetrazolinone compound 81 and Compound VI in the ratio of 1/1;

a composition for controlling plant diseases comprising any one of compounds selected from the present tetrazolinone compound 1 to the present tetrazolinone compound 81 and Compound VI in the ratio of 10/1;

a composition for controlling plant diseases comprising any one of compounds selected from the present tetrazolinone compound 1 to the present tetrazolinone compound 81 and Compound VII in the ratio of 0.1/1;

a composition for controlling plant diseases comprising any one of compounds selected from the present tetrazolinone compound 1 to the present tetrazolinone compound 81 and Compound VII in the ratio of 1/1;

a composition for controlling plant diseases comprising any one of compounds selected from the present tetrazolinone compound 1 to the present tetrazolinone compound 81 and Compound VII in the ratio of 10/1;

a composition for controlling plant diseases comprising any one of compounds selected from the present tetrazolinone compound 1 to the present tetrazolinone compound 81 and Compound VIII in the ratio of 0.1/1;

a composition for controlling plant diseases comprising any one of compounds selected from the present tetrazolinone compound 1 to the present tetrazolinone compound 81 and Compound VIII in the ratio of 1/1;

a composition for controlling plant diseases comprising any one of compounds selected from the present tetrazolinone compound 1 to the present tetrazolinone compound 81 and Compound VIII in the ratio of 10/1;

a composition for controlling plant diseases comprising any one of compounds selected from the present tetrazolinone compound 1 to the present tetrazolinone compound 81 and Compound IX in the ratio of 0.1/1;

a composition for controlling plant diseases comprising any one of compounds selected from the present tetrazolinone compound 1 to the present tetrazolinone compound 81 and Compound IX in the ratio of 1/1;

a composition for controlling plant diseases comprising any one of compounds selected from the present tetrazolinone compound 1 to the present tetrazolinone compound 81 and Compound IX in the ratio of 10/1;

a composition for controlling plant diseases comprising any one of compounds selected from the present tetrazolinone compound 1 to the present tetrazolinone compound 81 and Compound X in the ratio of 0.1/1;

a composition for controlling plant diseases comprising any one of compounds selected from the present tetrazolinone compound 1 to the present tetrazolinone compound 81 and Compound X in the ratio of 1/1;

a composition for controlling plant diseases comprising any one of compounds selected from the present tetrazolinone compound 1 to the present tetrazolinone compound 81 and Compound X in the ratio of 10/1;

a composition for controlling plant diseases comprising any one of compounds selected from the present tetrazolinone compound 1 to the present tetrazolinone compound 81 and Compound XI in the ratio of 0.1/1;

a composition for controlling plant diseases comprising any one of compounds selected from the present tetrazolinone compound 1 to the present tetrazolinone compound 81 and Compound XI in the ratio of 1/1;

a composition for controlling plant diseases comprising any one of compounds selected from the present tetrazolinone compound 1 to the present tetrazolinone compound 81 and Compound XI in the ratio of 10/1;

a composition for controlling plant diseases comprising any one of compounds selected from the present tetrazolinone compound 1 to the present tetrazolinone compound 81 and Compound XII in the ratio of 0.1/1;

a composition for controlling plant diseases comprising any one of compounds selected from the present tetrazolinone compound 1 to the present tetrazolinone compound 81 and Compound XII in the ratio of 1/1;

a composition for controlling plant diseases comprising any one of compounds selected from the present tetrazolinone compound 1 to the present tetrazolinone compound 81 and Compound XII in the ratio of 10/1;

a composition for controlling plant diseases comprising any one of compounds selected from the present tetrazolinone compound 1 to the present tetrazolinone compound 81 and Compound XIII in the ratio of 0.1/1;

a composition for controlling plant diseases comprising any one of compounds selected from the present tetrazolinone compound 1 to the present tetrazolinone compound 81 and Compound XIII in the ratio of 1/1;

a composition for controlling plant diseases comprising any one of compounds selected from the present tetrazolinone compound 1 to the present tetrazolinone compound 81 and Compound XIII in the ratio of 10/1;

a composition for controlling plant diseases comprising any one of compounds selected from the present tetrazolinone compound 1 to the present tetrazolinone compound 81 and Compound XIV in the ratio of 0.1/1;

a composition for controlling plant diseases comprising any one of compounds selected from the present tetrazolinone compound 1 to the present tetrazolinone compound 81 and Compound XIV in the ratio of 1/1;

a composition for controlling plant diseases comprising any one of compounds selected from the present tetrazolinone compound 1 to the present tetrazolinone compound 81 and Compound XIV in the ratio of 10/1;

a composition for controlling plant diseases comprising any one of compounds selected from the present tetrazolinone compound 1 to the present tetrazolinone compound 81 and Compound XV in the ratio of 0.1/1;

a composition for controlling plant diseases comprising any one of compounds selected from the present tetrazolinone compound 1 to the present tetrazolinone compound 81 and Compound XV in the ratio of 1/1;

a composition for controlling plant diseases comprising any one of compounds selected from the present tetrazolinone compound 1 to the present tetrazolinone compound 81 and Compound XV in the ratio of 10/1;

a composition for controlling plant diseases comprising any one of compounds selected from the present tetrazolinone compound 1 to the present tetrazolinone compound 81 and Compound XVI in the ratio of 0.1/1;

a composition for controlling plant diseases comprising any one of compounds selected from the present tetrazolinone compound 1 to the present tetrazolinone compound 81 and Compound XVI in the ratio of 1/1;

a composition for controlling plant diseases comprising any one of compounds selected from the present tetrazolinone compound 1 to the present tetrazolinone compound 81 and Compound XVI in the ratio of 10/1;

a composition for controlling plant diseases comprising any one of compounds selected from the present tetrazolinone compound 1 to the present tetrazolinone compound 81 and Compound XVII in the ratio of 0.1/1;

a composition for controlling plant diseases comprising any one of compounds selected from the present tetrazolinone compound 1 to the present tetrazolinone compound 81 and Compound XVII in the ratio of 1/1;

a composition for controlling plant diseases comprising any one of compounds selected from the present tetrazolinone compound 1 to the present tetrazolinone compound 81 and Compound XVII in the ratio of 10/1;

a composition for controlling plant diseases comprising any one of compounds selected from the present tetrazolinone compound 1 to the present tetrazolinone compound 81 and Compound XVIII in the ratio of 0.1/1;

a composition for controlling plant diseases comprising any one of compounds selected from the present tetrazolinone compound 1 to the present tetrazolinone compound 81 and Compound XVIII in the ratio of 1/1; and a composition for controlling plant diseases comprising any one of compounds selected from the present tetrazolinone compound 1 to the present tetrazolinone compound 81 and Compound XVIII in the ratio of 10/1.

Next, the Formulation Examples are shown below. The term "part(s)" means "part(s) by weight".

Formulation Example 1

Fifty (50) parts of any one of the above-mentioned composition of the present inventions, 3 parts of calcium lignosulfonate, 2 parts of magnesium lauryl sulfate and 45 parts of synthetic hydrated silicon dioxide are well mixed while grinding to obtain a formulation.

Formulation Example 2

Twenty (20) parts of any one of the above-mentioned composition of the present inventions, 1.5 parts of sorbitan trioleate are mixed with 28.5 parts of an aqueous solution containing 2 parts of polyvinyl alcohol, and the mixture is then finely-ground by a wet grinding method. To this mixture is then added 40 parts of an aqueous solution containing 0.05 parts of xanthane gum and 0.1 parts of magnesium aluminium silicate, and 10 parts of propylene glycol is further added thereto. The mixture is stirred to obtain a formulation.

Formulation Example 3

Two (2) parts of any one of the above-mentioned composition of the present inventions, 88 parts of kaolin clay and 10 parts of talc are mixed-grinding to obtain a formulation.

Formulation Example 4

Five (5) parts of any one of the above-mentioned composition of the present inventions, 14 parts of polyoxyethylene styryl phenyl ether, 6 parts of calcium dodecylbenzene sulfonate and 75 parts of xylene are mixed-grinding to obtain a formulation.

Formulation Example 5

Two (2) parts of any one of the above-mentioned composition of the present inventions, one part of synthetic hydrated silicon dioxide, 2 parts of calcium lignosulfonate, 30 parts of bentonite and 65 parts of kaolin clay are mixed-grinding and thereto is added water and the mixture is well kneaded and is then granulated and dried to obtain a formulation.

Formulation Example 6

Ten (10) parts of any one of the above-mentioned composition of the present inventions, 35 parts of white carbon containing 50 parts of ammonium polyoxyethylene alkyl ether sulfate, and 55 parts of water are mixed, and the mixture is then finely-ground by a wet grinding method to obtain a formulation.

Next, Test examples are used to show an efficacy of the composition of the present invention on controlling plant diseases.

Here the control effects were evaluated by visually observing a lesion area on the tested plants when examined and followed by comparing the lesion area of the plants treated with the composition of the present invention with a lesion area of the untreated plants.

The "Efficacy" in each test means a value calculated by the following "Equation 1", and it is ranked depending on its numerical value as shown in Table 5.

$$\text{Efficacy} = 100 \times (X-Y)/X \qquad \text{"Equation 1"}$$

where

X: Degree of fungal growth in non-treated area

Y: Degree of fungal growth in treated area

TABLE 5

| Efficacy | Efficacy Rank |
|---|---|
| more than 95 | A |
| 80 or more to less than 95 | B |
| 50 or more to less than 80 | C |
| 30 or more to less than 50 | D |
| less than 30 | E |

Test Example 1

Control Test Against Wheat Leaf Blotch (*Septoria tritici*)

Each of the testing compounds was diluted with dimethyl sulfoxide (DMSO) to the prescribed concentration, respectively, and each DMSO solution of the testing compounds was dispensed into a titer plate (with 96 wells) in the amount of 1 μl. Thereto was then dispensed 150 μl of a potato dextrose broth to which conidia of wheat leaf blight fungus were inoculated in advance. This plate was cultured at 18° C. for four days, thereby allowing wheat leaf blight fungus to undergo proliferation, and the absorbance at 550 nm of each well of the titer plate was then measured to determine a degree of growth of the wheat leaf blight fungus. The efficacy was calculated from the obtained degree of growth by the above-mentioned "Equation 1", and was then ranked according to [Table 5]. The test results are shown in the following Table 6 to Table 16.

TABLE 6

| Present tetrazolinone compound | Concentration (ppm) | Present carboxamide compound | Concentration (ppm) | Efficacy Rank |
|---|---|---|---|---|
| Present tetrazolinone compound 1 | 3 | Compound I | 1 | A |
| Present tetrazolinone compound 1 | 1 | Compound I | 3 | A |
| Present tetrazolinone compound 1 | 3 | Compound II | 1 | A |
| Present tetrazolinone compound 1 | 1 | Compound II | 3 | A |
| Present tetrazolinone compound 1 | 3 | Compound III | 1 | A |
| Present tetrazolinone compound 1 | 1 | Compound III | 3 | A |
| Present tetrazolinone compound 1 | 3 | Compound IV | 1 | A |
| Present tetrazolinone compound 1 | 1 | Compound IV | 3 | A |
| Present tetrazolinone compound 1 | 3 | Compound V | 1 | A |
| Present tetrazolinone compound 1 | 1 | Compound V | 3 | A |
| Present tetrazolinone compound 1 | 3 | Compound VI | 1 | A |
| Present tetrazolinone compound 1 | 1 | Compound VI | 3 | A |

TABLE 7

| Present tetrazolinone compound | Concentration (ppm) | Present carboxamide compound | Concentration (ppm) | Efficacy Rank |
|---|---|---|---|---|
| Present tetrazolinone compound 2 | 3 | Compound I | 1 | A |
| Present tetrazolinone compound 2 | 1 | Compound I | 3 | A |
| Present tetrazolinone compound 2 | 3 | Compound II | 1 | A |
| Present tetrazolinone compound 2 | 1 | Compound II | 3 | A |
| Present tetrazolinone compound 2 | 3 | Compound III | 1 | A |
| Present tetrazolinone compound 2 | 1 | Compound III | 3 | A |
| Present tetrazolinone compound 2 | 3 | Compound IV | 1 | A |
| Present tetrazolinone compound 2 | 1 | Compound IV | 3 | A |
| Present tetrazolinone compound 2 | 3 | Compound V | 1 | A |
| Present tetrazolinone compound 2 | 1 | Compound V | 3 | A |
| Present tetrazolinone compound 2 | 3 | Compound VI | 1 | A |
| Present tetrazolinone compound 2 | 1 | Compound VI | 3 | A |

TABLE 8

| Present tetrazolinone compound | Concentration (ppm) | Present carboxamide compound | Concentration (ppm) | Efficacy Rank |
|---|---|---|---|---|
| Present tetrazolinone compound 3 | 3 | Compound I | 1 | A |
| Present tetrazolinone compound 3 | 1 | Compound I | 3 | A |
| Present tetrazolinone compound 3 | 3 | Compound II | 1 | A |
| Present tetrazolinone compound 3 | 1 | Compound II | 3 | A |
| Present tetrazolinone compound 3 | 3 | Compound III | 1 | A |

TABLE 8-continued

| Present tetrazolinone compound | Concentration (ppm) | Present carboxamide compound | Concentration (ppm) | Efficacy Rank |
|---|---|---|---|---|
| Present tetrazolinone compound 3 | 1 | Compound III | 3 | A |
| Present tetrazolinone compound 3 | 3 | Compound IV | 1 | A |
| Present tetrazolinone compound 3 | 1 | Compound IV | 3 | A |
| Present tetrazolinone compound 3 | 3 | Compound V | 1 | A |
| Present tetrazolinone compound 3 | 1 | Compound V | 3 | A |
| Present tetrazolinone compound 3 | 3 | Compound VI | 1 | A |
| Present tetrazolinone compound 3 | 1 | Compound VI | 3 | A |

TABLE 9

| Present tetrazolinone compound | Concentration (ppm) | Present carboxamide compound | Concentration (ppm) | Efficacy Rank |
|---|---|---|---|---|
| Present tetrazolinone compound 4 | 3 | Compound I | 1 | A |
| Present tetrazolinone compound 4 | 1 | Compound I | 3 | A |
| Present tetrazolinone compound 4 | 3 | Compound II | 1 | A |
| Present tetrazolinone compound 4 | 1 | Compound II | 3 | A |
| Present tetrazolinone compound 4 | 3 | Compound III | 1 | A |
| Present tetrazolinone compound 4 | 1 | Compound III | 3 | A |
| Present tetrazolinone compound 4 | 3 | Compound IV | 1 | A |
| Present tetrazolinone compound 4 | 1 | Compound IV | 3 | A |
| Present tetrazolinone compound 4 | 3 | Compound V | 1 | A |
| Present tetrazolinone compound 4 | 1 | Compound V | 3 | A |
| Present tetrazolinone compound 4 | 3 | Compound VI | 1 | A |
| Present tetrazolinone compound 4 | 1 | Compound VI | 3 | A |

TABLE 10

| Present tetrazolinone compound | Concentration (ppm) | Present carboxamide compound | Concentration (ppm) | Efficacy Rank |
|---|---|---|---|---|
| Present tetrazolinone compound 5 | 3 | Compound I | 1 | A |
| Present tetrazolinone compound 5 | 1 | Compound I | 3 | A |
| Present tetrazolinone compound 5 | 3 | Compound II | 1 | A |
| Present tetrazolinone compound 5 | 1 | Compound II | 3 | A |
| Present tetrazolinone compound 5 | 3 | Compound III | 1 | A |
| Present tetrazolinone compound 5 | 1 | Compound III | 3 | A |
| Present tetrazolinone compound 5 | 3 | Compound IV | 1 | A |
| Present tetrazolinone compound 5 | 1 | Compound IV | 3 | A |
| Present tetrazolinone compound 5 | 3 | Compound V | 1 | A |
| Present tetrazolinone compound 5 | 1 | Compound V | 3 | A |
| Present tetrazolinone compound 5 | 3 | Compound VI | 1 | A |
| Present tetrazolinone compound 5 | 1 | Compound VI | 3 | A |

TABLE 11

| Present tetrazolinone compound | Concentration (ppm) | Present carboxamide compound | Concentration (ppm) | Efficacy Rank |
|---|---|---|---|---|
| Present tetrazolinone compound 6 | 3 | Compound I | 1 | A |
| Present tetrazolinone compound 6 | 1 | Compound I | 3 | A |
| Present tetrazolinone compound 6 | 3 | Compound II | 1 | A |
| Present tetrazolinone compound 6 | 1 | Compound II | 3 | A |
| Present tetrazolinone compound 6 | 3 | Compound III | 1 | A |
| Present tetrazolinone compound 6 | 1 | Compound III | 3 | A |
| Present tetrazolinone compound 6 | 3 | Compound IV | 1 | A |
| Present tetrazolinone compound 6 | 1 | Compound IV | 3 | A |
| Present tetrazolinone compound 6 | 3 | Compound V | 1 | A |
| Present tetrazolinone compound 6 | 1 | Compound V | 3 | A |

TABLE 11-continued

| Present tetrazolinone compound | Concentration (ppm) | Present carboxamide compound | Concentration (ppm) | Efficacy Rank |
|---|---|---|---|---|
| Present tetrazolinone compound 6 | 3 | Compound VI | 1 | A |
| Present tetrazolinone compound 6 | 1 | Compound VI | 3 | A |

TABLE 12

| Present tetrazolinone compound | Concentration (ppm) | Present carboxamide compound | Concentration (ppm) | Efficacy Rank |
|---|---|---|---|---|
| Present tetrazolinone compound 7 | 3 | Compound I | 1 | A |
| Present tetrazolinone compound 7 | 1 | Compound I | 3 | A |
| Present tetrazolinone compound 7 | 3 | Compound II | 1 | A |
| Present tetrazolinone compound 7 | 1 | Compound II | 3 | A |
| Present tetrazolinone compound 7 | 3 | Compound III | 1 | A |
| Present tetrazolinone compound 7 | 1 | Compound III | 3 | A |
| Present tetrazolinone compound 7 | 3 | Compound IV | 1 | A |
| Present tetrazolinone compound 7 | 1 | Compound IV | 3 | A |
| Present tetrazolinone compound 7 | 3 | Compound V | 1 | A |
| Present tetrazolinone compound 7 | 1 | Compound V | 3 | A |
| Present tetrazolinone compound 7 | 3 | Compound VI | 1 | A |
| Present tetrazolinone compound 7 | 1 | Compound VI | 3 | A |

TABLE 13

| Present tetrazolinone compound | Concentration (ppm) | Present carboxamide compound | Concentration (ppm) | Efficacy Rank |
|---|---|---|---|---|
| Present tetrazolinone compound 8 | 3 | Compound I | 1 | A |
| Present tetrazolinone compound 8 | 1 | Compound I | 3 | A |
| Present tetrazolinone compound 8 | 3 | Compound II | 1 | A |
| Present tetrazolinone compound 8 | 1 | Compound II | 3 | A |
| Present tetrazolinone compound 8 | 3 | Compound III | 1 | A |
| Present tetrazolinone compound 8 | 1 | Compound III | 3 | A |
| Present tetrazolinone compound 8 | 3 | Compound IV | 1 | A |
| Present tetrazolinone compound 8 | 1 | Compound IV | 3 | A |
| Present tetrazolinone compound 8 | 3 | Compound V | 1 | A |
| Present tetrazolinone compound 8 | 1 | Compound V | 3 | A |
| Present tetrazolinone compound 8 | 3 | Compound VI | 1 | A |
| Present tetrazolinone compound 8 | 1 | Compound VI | 3 | A |

TABLE 14

| Present tetrazolinone compound | Concentration (ppm) | Present carboxamide compound | Concentration (ppm) | Efficacy Rank |
|---|---|---|---|---|
| Present tetrazolinone compound 9 | 3 | Compound I | 1 | A |
| Present tetrazolinone compound 9 | 1 | Compound I | 3 | A |
| Present tetrazolinone compound 9 | 3 | Compound II | 1 | A |
| Present tetrazolinone compound 9 | 1 | Compound II | 3 | A |
| Present tetrazolinone compound 9 | 3 | Compound III | 1 | A |
| Present tetrazolinone compound 9 | 1 | Compound III | 3 | A |
| Present tetrazolinone compound 9 | 3 | Compound IV | 1 | A |
| Present tetrazolinone compound 9 | 1 | Compound IV | 3 | A |
| Present tetrazolinone compound 9 | 3 | Compound V | 1 | A |
| Present tetrazolinone compound 9 | 1 | Compound V | 3 | A |
| Present tetrazolinone compound 9 | 3 | Compound VI | 1 | A |
| Present tetrazolinone compound 9 | 1 | Compound VI | 3 | A |

TABLE 15

| Present tetrazolinone compound | Concentration (ppm) | Present carboxamide compound | Concentration (ppm) | Efficacy Rank |
|---|---|---|---|---|
| Present tetrazolinone compound 10 | 3 | Compound I | 1 | A |
| Present tetrazolinone compound 10 | 1 | Compound I | 3 | A |
| Present tetrazolinone compound 10 | 3 | Compound II | 1 | A |
| Present tetrazolinone compound 10 | 1 | Compound II | 3 | A |
| Present tetrazolinone compound 10 | 3 | Compound III | 1 | A |
| Present tetrazolinone compound 10 | 1 | Compound III | 3 | A |
| Present tetrazolinone compound 10 | 3 | Compound IV | 1 | A |
| Present tetrazolinone compound 10 | 1 | Compound IV | 3 | A |
| Present tetrazolinone compound 10 | 3 | Compound V | 1 | A |
| Present tetrazolinone compound 10 | 1 | Compound V | 3 | A |
| Present tetrazolinone compound 10 | 3 | Compound VI | 1 | A |
| Present tetrazolinone compound 10 | 1 | Compound VI | 3 | A |

TABLE 16

| Present tetrazolinone compound | Concentration (ppm) | Present carboxamide compound | Concentration (ppm) | Efficacy Rank |
|---|---|---|---|---|
| Present tetrazolinone compound 11 | 3 | Compound I | 1 | A |
| Present tetrazolinone compound 11 | 1 | Compound I | 3 | A |
| Present tetrazolinone compound 11 | 3 | Compound II | 1 | A |
| Present tetrazolinone compound 11 | 1 | Compound II | 3 | A |
| Present tetrazolinone compound 11 | 3 | Compound III | 1 | A |
| Present tetrazolinone compound 11 | 1 | Compound III | 3 | A |
| Present tetrazolinone compound 11 | 3 | Compound IV | 1 | A |
| Present tetrazolinone compound 11 | 1 | Compound IV | 3 | A |
| Present tetrazolinone compound 11 | 3 | Compound V | 1 | A |
| Present tetrazolinone compound 11 | 1 | Compound V | 3 | A |
| Present tetrazolinone compound 11 | 3 | Compound VI | 1 | A |
| Present tetrazolinone compound 11 | 1 | Compound VI | 3 | A |

INDUSTRIAL APPLICABILITY

The present invention can control plant diseases.

The invention claimed is:

1. A composition for controlling plant diseases comprising a tetrazolinone compound represented by a formula (1):

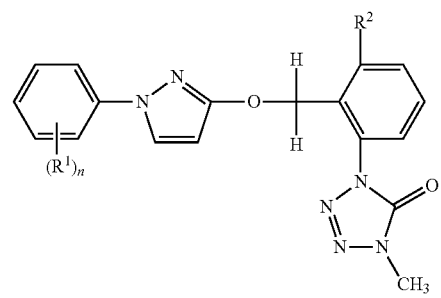

wherein
n is an integer of any one of 0 to 5;
$R^1$ represents a halogen atom, a C1-C6 alkyl group, a C1-C6 alkoxy group, a C1-C6 alkylthio group, a nitro group or a cyano group;
$R^2$ represents a C1-C3 alkyl group, a C3-C4 cycloalkyl group, a halogen atom, a C1-C3 alkoxy group, a C1-C2 alkylthio group, a C2-C3 alkenyl group, or a C2-C3 alkynyl group,
the $R^1$ or $R^2$ can have independently halogen atom(s) in the alkyl moiety;
with the proviso that when n is an integer of 2 or more, two or more of the $R^1$ may be different from each other,
and one or more carboxamide compounds selected from the Group (A):

Group (A): a group consisting of bixafen, benzovindiflupyr, fluxapyroxad, penthiopyrad, N-(1,1,3-trimethylindan-4-yl)-1-methyl-3-difluoromethylpyrazole-4-carboxylic acid amide, a compound represented by the following formula (b):

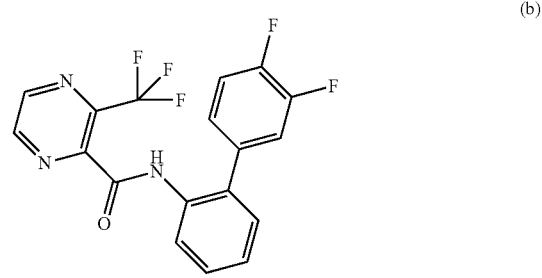 [SMILES: O=C(Nc1ccccc1-c1ccc(F)c(F)c1)c1nccnc1C(F)(F)F]

isofetamid, isopyrazam, boscalid, fluopyram, sedaxane, penflufen, flutolanil, mepronil, carboxin, thifluzamide, and furametpyr.

2. The composition for controlling plant diseases according to claim 1 wherein a weight ratio of the tetrazolinone compound to the carboxamide compound is that of the tetrazolinone compound/the carboxamide compound=0.1/1 to 10/1.

3. A method for controlling plant diseases which comprises applying each effective amount of a tetrazolinone compound represented by a formula (1):

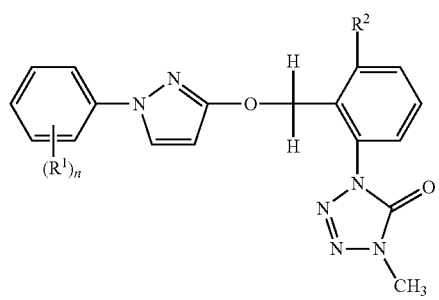

(1)

wherein
n is an integer of any one of 0 to 5;
$R^1$ represents a halogen atom, a C1-C6 alkyl group, a C1-C6 alkoxy group, a C1-C6 alkylthio group, a nitro group or a cyano group;
$R^2$ represents a C1-C3 alkyl group, a C3-C4 cycloalkyl group, a halogen atom, a C1-C3 alkoxy group, a C1-C2 alkylthio group, a C2-C3 alkenyl group, or a C2-C3 alkynyl group,
the $R^1$ or $R^2$ can have independently halogen atom(s) in the alkyl moiety;

with the proviso that when n is an integer of 2 or more, two or more of the $R^1$ may be different from each other, and one or more carboxamide compounds selected from the Group (A):

Group (A): a group consisting of bixafen, benzovindiflupyr, fluxapyroxad, penthiopyrad, N-(1,1,3-trimethylindan-4-yl)-1-methyl-3-difluoromethylpyrazole-4-carboxylic acid amide, a compound represented by the following formula (b):

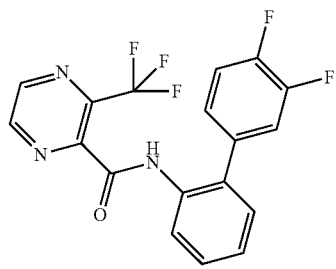

(b)

isofetamid, isopyrazam, boscalid, fluopyram, sedaxane, penflufen, flutolanil, mepronil, carboxin, thifluzamide, and furametpyr,
to a plant or a soil for cultivating the plant.

4. The method for controlling plant diseases according to claim 3 wherein a weight ratio of the tetrazolinone compound to the carboxamide compound is that of the tetrazolinone compound/the carboxamide compound=0.1/1 to 10/1.

5. The method for controlling plant diseases according to claim 3 wherein the plant or the soil for cultivating the plant is wheat or the soil for cultivating wheat, respectively.

* * * * *